United States Patent
Dean et al.

(10) Patent No.: US 11,402,364 B1
(45) Date of Patent: Aug. 2, 2022

(54) APPARATUS FOR THE DETECTION, ASSESSMENT AND MITIGATION OF CYANOBACTERIA IN REAL TIME AND METHOD OF USING THE SAME

(71) Applicant: Eget Liber, Inc., Syracuse, NY (US)

(72) Inventors: Jason A. Dean, Kirkville, NY (US); Joseph B. Milstein, Brookline, MA (US)

(73) Assignee: EGET LIBER, INC., Kirkville, NY (US)

( * ) Notice: Subject to any disclaimer, the term of this patent is extended or adjusted under 35 U.S.C. 154(b) by 0 days.

(21) Appl. No.: 17/672,176

(22) Filed: Feb. 15, 2022

Related U.S. Application Data

(60) Provisional application No. 63/302,766, filed on Jan. 25, 2022, provisional application No. 63/149,707, filed on Feb. 16, 2021.

(51) Int. Cl.
*G01N 33/18* (2006.01)
*G01N 21/31* (2006.01)

(52) U.S. Cl.
CPC ............. *G01N 33/18* (2013.01); *G01N 21/31* (2013.01); *G01N 2201/1293* (2013.01)

(58) Field of Classification Search
CPC . G01N 33/18; G01N 21/31; G01N 2201/1293
See application file for complete search history.

(56) References Cited

U.S. PATENT DOCUMENTS

| | | | | |
|---|---|---|---|---|
| 2003/0155228 A1* | 8/2003 | Mills | .................. | B01D 53/72 422/186.3 |
| 2010/0279373 A1* | 11/2010 | Cordemans de Meulenaer | .......... | B01J 19/10 435/173.1 |

FOREIGN PATENT DOCUMENTS

| | | | | |
|---|---|---|---|---|
| CN | 203781863 U | * | 8/2014 | ............... C02F 1/00 |
| KR | 1020160031766 A | * | 3/2016 | ............... C02F 1/40 |

* cited by examiner

*Primary Examiner* — Jamil Ahmed
(74) *Attorney, Agent, or Firm* — Joseph B. Milstein, PC; Joseph B. Milstein

(57) ABSTRACT

The invention relates to the detection, assessment and mitigation of harmful water-borne bacteria such as cyanobacteria. Multiple apparatus embodiments and variations are described. One apparatus can apply at least one of UV-C irradiation, microbubbles containing ozone and ultrasonic sound to mitigate the harmful water-borne bacteria. The systems and methods of the invention can be applied to bodies of water, including fresh water and salt water, and can be applied to wastewater treatment. The systems and methods of the invention can be used to reduce the concentration of algae directly and can be used to reduce the concentration of nutrients in water that algae use to grow. Methods of mitigation of the harmful bacteria are described that do not involve the introduction of chemicals into the environment.

10 Claims, 13 Drawing Sheets

APPARATUS FOR THE DETECTION, ASSESSMENT AND MITIGATION OF CYANOBACTERIA IN REAL TIME AND METHOD OF USING THE SAME

CROSS-REFERENCE TO RELATED APPLICATIONS

This application claims priority to and the benefit of U.S. provisional patent application Ser. No. 63/149,707, filed Feb. 16, 2021, and claims priority to and the benefit of U.S. provisional patent application Ser. No. 63/302,766, filed Jan. 25, 2022, each of which applications is incorporated herein by reference in its entirety.

FIELD OF THE INVENTION

The invention relates to the detection, assessment and mitigation of cyanobacteria in general and particularly to systems and methods for detecting, assessing and mitigating cyanobacteria in real time.

BACKGROUND OF THE INVENTION

The Centers for Disease Control (CDC) has recently launched a Harmful Algal Bloom (HAB) website in order to track widespread cyanobacteria bloom outbreaks nationally. A recent report from 2016 indicated harmful algal blooms outbreaks in 17 states in the month of September alone.

According to the CDC, algal blooms are quickly becoming a public health issue, resulting in symptoms ranging from mild to severe. Typical symptoms of HAB toxins include skin irritation, stomach and intestinal cramping, lung and central nervous system impairments. HAB toxins are harmful to both humans and animals.

Cyanobacteria blooms form when water is both warm and nutrient rich, for example from fertilizer runoff. The blooms typically appear in mid to late summer as the bodies of water begin to warm. Nutrients such as phosphorus and nitrogen help to feed this bacterium, which typically multiply during the night and rise to spread across a water's surface.

The appearance of cyanobacterium blooms often resembles floating green paint, which often give off a strong odor when they die. The blooms often block out light that organisms require to thrive in the water, as well as to deplete the water source of valuable oxygen. Cyanobacterium often produce cyanotoxins, which are dangerous natural toxins that cause a variety of harmful effects in both humans and animals.

Excessive algal growth as a result of an increase in growth factors needed to support photosynthesis, also known as eutrophication, causes an estimated at $2.2 billion dollars in damage annually in the U.S. alone. Often these damages are the result of blooms of blue green algae, also known as cyanobacteria, which contaminate drinking water supplies and recreational areas.

A typical consequence of vast blue green algae blooms is the foul odor that often emanates from decomposing algae as they die off. These dense blooms often block out the sunlight that is needed to help support organisms that typical thrive in the water, but become starved from sunlight as a result of the dense coverage that often lay on the surface of the water. As the algae die off, often-inorganic carbon is depleted that results in an increase in water pH levels. An additional consequence of decomposition is the depletion of dissolved oxygen, a factor that has been known to create hypoxic or anoxic conditions that are unable to support life.

More recently, hypoxic events have been found along marine coastal environments, such as those found along the Mississippi River, Gulf of Mexico, Susquehanna River, and Chesapeake Bay, which endanger lucrative commercial and recreational fisheries. These hypoxic events often impact large areas, for example approximately 245,000 square kilometers in these same areas. Of course, these events are not only limited to coastal marine areas, but they have also been found in many freshwater lakes as well, such as Lake Erie.

Recently an exceptionally hot weather pattern has pushed water temperatures in most of the Great Lakes to the highest levels on record so early in the summer. Over lakes Erie and Ontario, the water is the warmest it has been since records began being kept, and could warm more in the coming weeks. The abnormally warm waters, consistent with climate-change trends in recent decades, could compromise water quality and harm marine life in some areas. Surface water temperatures averaged over all of the Great Lakes, except the deep and choppy Lake Superior, have risen well into the 70 s while Lake Erie has flirted with 80 degrees.

Blue-green algae or cyanobacteria over western waters of Lake Erie in early July 2020. The foul-smelling algal blooms can harm fish and make people who are exposed to the water sick. In 2014, cyanobacteria from Lake Erie entered the water supply in Toledo, and residents were ordered not to drink or touch the water. The jump-start to the algal bloom due to the warm water temperatures means it will be around for several weeks longer than normal. The earliest observed algae blooms in the Great Lakes occurred in June in 2018.

Specific conditions which support the growth of algae blooms include water which embodies thermal stratification. This occurs when the upper layer of water is warmer than the lower layers, which often occurs when the two thermal layers stop mixing. This reduced thermal mixing often occurs when the waters are calm.

In the last decade, Lake Erie has experienced repeated harmful cyanobacteria blooms (cHABs) and cyanotoxins that have likely resulted in probable cases of human illness. A prevalent toxigenic cyanobacterium has been the *Microcystis* genus, which are known to produce microcystins. Furthermore, other cyanotoxins have also been identified, such as anatoxin-a, that implicate the presence of other toxigenic cyanobacteria like *Anabaena* (Dolichospermum) and *Lyngbya*.

The cells of cyanobacterium (*Anabaena flos-aquae*), are capable of producing neurotoxins, which have the capacity to interfere with the central nervous system. These neurotoxins can disrupt the communication between neurons and muscle cells, which can lead to death by causing paralysis of respiratory muscles.

Not all cyanobacteria produce blue-green algae, but some result in "red tides" or red water blooms. The same methods of the invention can be deployed against these bacteria as well.

Cyanotoxins are classified based on two criteria: (1) by their action mechanism in land vertebrates, which are broken into 3 sub-groups; hepatoxins, neurotoxins, and dermatotoxins; and (2) their overall chemical structure, which is also broken into 3 sub-groups; cyclic peptides, alkaloids, or lipopolysaccharides (LPS).

Hepatoxins can cause the rupture of structures within the liver by means of hypovolemic shock, resulting in excessive accumulation of blood within the liver. Hepatoxins can also interfere with the control of cellular structure and function of the liver by inhibiting protein phosphatases type 1 or 2 (PP1 or PP2A).

The most toxic compounds often produced by cyanobacteria are known as neurotoxins. These toxins can cause paralysis of the respiratory muscles by interfering with the neuromuscular system, which has been shown to cause death in laboratory rats in just minutes. One such neurotoxin are the saxitoxin type, also referred to as PSPs (paralytic shellfish poisoning), mainly due to how this toxin was first identified from humans consuming contaminated bivalve mollusks. These same toxins were also found to be the result of what has become known as the "red tide" phenomenon.

Cyanotoxins that are classified as dermatotoxins, aplysiatoxins and lyngbiatoxins have each been identified in marine cyanobacteria, which have been known to cause severe dermatitis for those who bath in coastal waters infected with the cyanobacteria.

In the prior art, chemical methods for controlling cyanobacteria growth have included the use of hydrogen-peroxide, which causes an oxidation process by which the hydrogen peroxide ($H_2O_2$) breaks down into water ($H_2O$) and pure oxygen ($O_2$), resulting in the death of exposed bacteria. The limitation here is that beneficial bacteria will also die as a result of its use, so great care is needed when employing this chemical agent. Another chemical method for controlling the spread of cyanobacteria is the use of antibiotics. Antibiotics such as Maracyn and Erythromycin have been found to be effective in killing cyanobacteria. Once more however the use of antibiotics to treat cyanobacteria will also interfere with the processes of beneficial bacteria as well.

Flesh eating bacteria have recently been identified as a problem in water, such as lakes, rivers, and the sea.

Standard Monitoring by Sampling a Body of Water

The standard procedure for sampling a body of water for Blue Green Algae ("BGA") involves taking a water sample, sending it to a laboratory for testing, and receiving back a report. This process can take one or more days to complete.

Errors may be introduced during the transport of the sample.

It is known that BGA can double their numbers every 3 days if the conditions are favorable. BGA samples are sensitive to temperature and lighting conditions.

If the sample is illuminated (for example if held in a transparent or translucent container) it may continue to grow BGA. If the sample is held in an opaque container it may lose BGA (because in the dark, if held for sufficient time, some of the BGA may die). The rate of growth may be affected by the temperature that the sample experiences.

The delay involved in transporting the sample to the laboratory may be variable from sample to sample.

In any event, the data returned in the report may be days old (which may not be the condition of the water at the time the results are obtained), and the result itself may not accurately represent the condition of the water at the time the sample was collected.

PATENT PRIOR ART

Also known in the prior art is de Meulenaer et al., U.S. Pat. No. 8,097,170, issued Jan. 17, 2012, which is said to disclose a device for treating liquid medium that has an ultrasound emitter located relative to a compartment of a container holding a liquid medium and a microbubble emitter located relative to the compartment. The ultrasound emitter emits high-frequency ultrasound between about 200 KHz and 10 MHz. The microbubble emitter emits bubbles with an average diameter of less than 1 mm.

Also known in the prior art is Kuwata et al., U.S. Pat. No. 8,849,483 issued Sep. 30, 2014, which is said to disclose systems and methods for operating autonomous waterborne vessels in a safe manner. The systems include hardware for identifying the locations and motions of other vessels, as well as the locations of stationary objects that represent navigation hazards. By applying a computational method that uses a maritime navigation algorithm for avoiding hazards and obeying COLREGS using Velocity Obstacles to the data obtained, the autonomous vessel computes a safe and effective path to be followed in order to accomplish a desired navigational end result, while operating in a manner so as to avoid hazards and to maintain compliance with standard navigational procedures defined by international agreement. The systems and methods have been successfully demonstrated on water with radar and stereo cameras as the perception sensors, and integrated with a higher level planner for trailing a maneuvering target.

Also known in the prior art is Song, et al., Korean published patent application KR 1020160031766A, published 23 Mar. 23, 2016, which is said to disclose a green tide removal apparatus using an UV-C lamp and an ultrasonic wave generator, which can prevent green tide by monitoring generation of cyanophyceae by measuring water quality of river, lake, etc., and by removing cyanophyceae during an initial stage of outbreak. The green tide removal apparatus of the present invention comprises: a main body having buoyancy so as to float on the water; an engine unit which generates power to move the main body; a power generation unit which generates electricity required to operate the engine unit; an analysis unit which measures water quality including population of cyanophyceae from a specimen obtained from corresponding waters; a treatment unit which removes cyanophyceae using ultrasonic waves and ultraviolet rays; a control unit which controls operation of the treatment unit depending on the population of cyanophycease measured from the analysis unit; and a communication unit which sends water quality data measured from the analysis unit to a control center so as to monitor generation of cyanophycease.

Also known in the prior art is Baltz, et al., U.S. Pat. No. 9,778,180, issued Oct. 3, 2017, which is said to disclose turbidometers and fluorometers having a unique form-factor to accommodate a number of optical components in a confined geometry. This provides the ability to compensate for change in light intensity from an optical source even in a closed-loop manner. The ability to package reference and signal detectors, along with a relatively large diameter LED light source in a confined geometry is particularly suited for applications requiring small-diameter sensors, such as multi-parameter sonde devices having a total diameter that is in the sub-two inch range. U.S. Pat. No. 10,393,654 issued Aug. 27, 2019 and U.S. Pat. No. 10,989,657 issued Apr. 27, 2021 issued from continuation applications of the above identified U.S. Pat. No. 9,778,180 and include similar disclosures.

There is a need for systems and methods to detect, to assess and to mitigate cyanobacteria and other harmful water borne bacteria in real time.

SUMMARY OF THE INVENTION

According to one aspect, the invention features an apparatus configured to mitigate a harmful water-borne bacteria, comprising: an aqueous monitoring sub-system configured to measure a concentration of algae in a body of water; an assessment sub-system in communication with the aqueous monitoring sub-system, the assessment sub-system comprising a microprocessor upon which can operate a set of instructions recorded in non-volatile memory, the assessment sub-system configured to provide a current value for a concentration of algae in the body of water, and configured to provide a predetermined reference concentration value; a control sub-system in communication with the aqueous monitoring sub-system and the assessment sub-system and configured to control the operation of the sub-systems, and to record data provided by the sub-systems; a mitigation sub-system comprising a UV illumination source, a source of microbubbles, and an ultrasonic transducer configured to apply, respectively, one or more of a UV illumination, a microbubble and ultrasonic sound to a quantity of the water to mitigate the growth of algae, in response to an instruction from the control sub-system; and a communication sub-system in communication with the control sub-system, the communication sub-system configured to transmit the data to an operator of the apparatus and to receive instructions for the operator for communication to the control sub-system.

In one embodiment, the apparatus is configured to reduce a concentration of a nutrient in the water to mitigate the growth of algae.

In one more embodiment, the nutrient in the water is phosphorus.

In still a further embodiment, the mitigation sub-system is configured to convert to molecular oxygen any of the ozone that remains after being applied to the quantity of water.

In another embodiment, the apparatus further comprises a flotation sub-system configured to allow the apparatus to operate as a water-going apparatus; a propulsion sub-system to allow the water-going apparatus to move relative to a body of water upon which it floats; a location sub-system configured to determine where the water-going apparatus is situated within the body of water; each of the flotation sub-system, the propulsion sub-system and the location sub-system in communication with the control sub-system.

In yet another embodiment, the apparatus further comprises an aerial observation sub-system tethered to the water-going apparatus and configured to provide information about the area adjacent the water-going apparatus, the aerial observation system in communication with the control sub-system.

In still another embodiment, the apparatus is configured to reduce the concentration of the algae directly.

According to another aspect, the invention relates to a method of mitigating a harmful water-borne bacterium, comprising the steps of: providing an apparatus comprising: an aqueous monitoring sub-system configured to measure a concentration of algae in a body of water; an assessment sub-system in communication with the aqueous monitoring sub-system, the assessment sub-system comprising a microprocessor upon which can operate a set of instructions recorded in non-volatile memory, the assessment sub-system configured to provide a current value for a concentration of algae in the body of water, and configured to provide a predetermined reference concentration value; a control sub-system in communication with the aqueous monitoring sub-system and the assessment sub-system and configured to control the operation of the sub-systems, and to record data provided by the sub-systems; a mitigation sub-system comprising a UV illumination source, a source of microbubbles, and an ultrasonic transducer configured to apply, respectively, one or more of a UV illumination, a microbubble and ultrasonic sound to a quantity of the water to mitigate the growth of algae, in response to an instruction from the control sub-system; and a communication sub-system in communication with the control sub-system, the communication sub-system configured to transmit the data to an operator of the apparatus and to receive instructions for the operator for communication to the control sub-system; operating the apparatus to collect a quantity of water; using the control sub-system to operate the mitigation sub-system to apply at least one of the UV illumination, the microbubble and the ultrasonic sound to the quantity of the water to reduce a concentration of a nutrient; thereby mitigating the harmful water-borne bacterium.

In yet another embodiment, the nutrient is phosphorus.

In still another embodiment, the mitigation sub-system performs the step of converting to molecular oxygen any of the ozone that remains after being applied to the quantity of water.

In one embodiment, the apparatus further comprises: a flotation sub-system configured to allow the apparatus to operate as a water-going apparatus; a propulsion sub-system to allow the water-going apparatus to move relative to a body of water upon which it floats; a location sub-system configured to determine where the water-going apparatus is situated within the body of water; each of the flotation sub-system, the propulsion sub-system and the location sub-system in communication with the control sub-system; and operating the water-going apparatus to reduce a concentration of the algae directly.

In another embodiment, the apparatus further comprises an aerial observation sub-system tethered to the water-going apparatus and configured to provide information about the area adjacent the water-going apparatus, the aerial observation system in communication with the control sub-system.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

Figure 1:
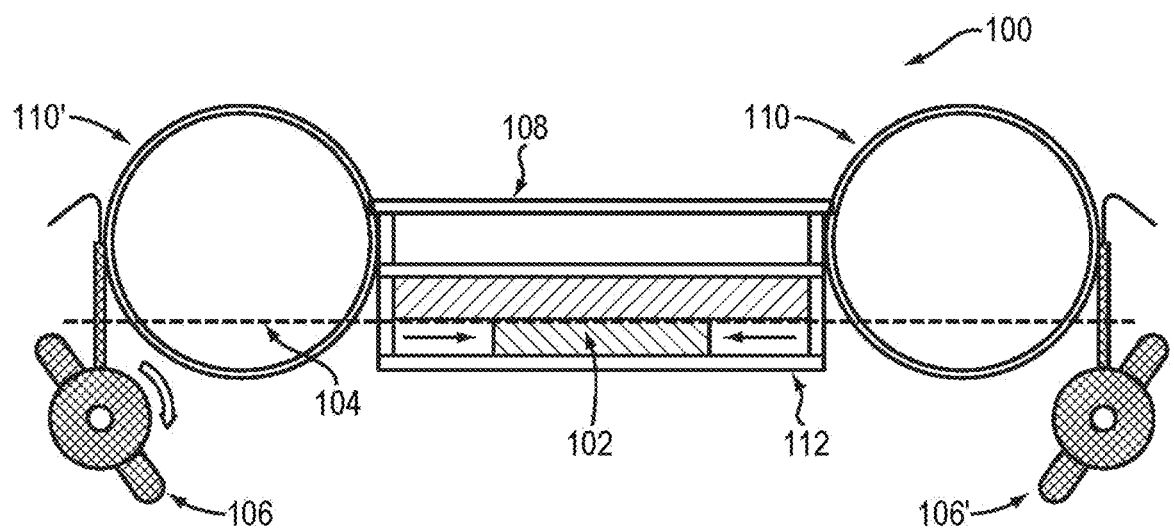
FIG. 1 depicts a cross section of one configuration of a cyanobacterium mitigating apparatus, which apparatus is capable of traversing water, supported by flotation assist pontoons.

The systems and methods according to principles of the invention include the following apparatus as sub-systems, which will be described in greater detail hereinbelow.

The apparatus includes a water-going apparatus having a flotation sub-system (such as a water-going vessel with flotation pontoons) and a propulsion sub-system (such as a motor), so that the water-going apparatus is configured to collect water containing harmful water-borne bacteria as a consequence of motion of the water-going apparatus relative to a body of water. In some embodiments, the apparatus includes a mitigation sub-system that can mitigate hazardous algae blooms (often referred to as "HABs") by the application of three processes, which can be applied singly or in combination: sonication of water containing algae using an ultrasonic source, illumination of the water containing algae with ultraviolet illumination (usually UV-C) and application of ozone to the water containing the algae, followed by deliberate destruction of any excess ozone using ultraviolet light in the vicinity of 254 nm. In some embodiments, the apparatus includes an aqueous monitoring sub-system comprising optical sensors for identifying the presence and concentration of algae in water by quantifying the amount of colored chemical species (such as Chlorophyll A, Phycocyanin (BGA-PC) and Phycoerythrin (BGA-PE)). The sensors have a resolution of 0.01 microgram per liter, a range of 0 to 1000 microgram/liter and a response time of under one second for each of the three species. In some embodiments, the apparatus includes an assessment sub-system which may be implemented in software (e.g., a set of instructions recorded on a non-volatile memory), which when operating on microprocessor-based hardware provides the capability of assessing the amount of algae present in the water that is being monitored by the aqueous monitoring sub-system, and which can compare the observed value with a predetermined reference value to provide a warning signal, for example that the algae concentration is high enough to be of concern, as appropriate. In some embodiments, additional optical sensors can be provided to measure the level of algae after mitigation in the water effluent that is discharged from the mitigation sub-system of the apparatus. In some embodiments, a feedback loop can be provided to allow the apparatus to change the parameters of operation of the mitigation sub-system to ensure that the algae are being properly mitigated. In some embodiments, the apparatus includes an aerial observation sub-system such as a tethered flying drone that is capable of providing visual data observed over a region adjacent to the water-going apparatus. In some embodiments, the apparatus includes a location sub-system system such as GPS so that its location can be ascertained, and so that it can be given instructions as to where to travel. In some embodiments, as part of the location sub-system, the water-going apparatus is capable of autonomous operation, for example as is described in U.S. Pat. No. 8,849,483 to Kuwata et al. In some embodiments, the apparatus includes a control sub-system comprising one or more controllers (for example based on microcontrollers or microprocessors) that allow each subsystem to be controlled, and a communication sub-system (such as a radio-based transmitter and receiver) to communicate to a user the status of each sub-system and associated data as may be needed, which data may be recorded, displayed or transmitted to another system or used for further processing and evaluation.

It is believed that the above described apparatus, without the flotation, propulsion and location sub-systems, can also be used to measure, evaluate and treat water that is conveyed to the apparats, for example, wastewater that is collected for treatment in conventional wastewater systems.

In general, the method of operation according to principles of the invention include the following steps or sub-operations. By way of example, this discussion will describe a fresh water body, such as a lake, but it is believed that the same methods can be applied with equal benefit to salt water bodies.

Conventional methods of detecting HABs include visual detection (e.g., observing a colored film or layer on the surface of a body of water), olfactory detection (e.g., smelling a foul odor emanating from a body of water), and by observation of injury or death to persons or animals that contact the water (e.g., dead fish floating in the water, persons or animals becoming sick by drinking or bathing in the water), followed by chemical analysis of water samples. By comparison, in the present invention, the use of optical sensors that respond to LED illumination (rather than ambient illumination) can detect the presence of algae in water at concentrations far below the concentrations needed so that the presence of HABs becomes apparent by visual or olfactory observation, or by observing damage to persons or animals. Therefore, one step in the processes of the invention includes using a monitoring sub-system that monitors the concentration of algae, and provides a warning signal or indication when the concentration of the algae reaches a predetermined reference value, which predetermined reference value may, for example, be a value lower than the concentration of algae in a HAB. Another step in the process is using a computer-based assessment sub-system that can assess the level of bacteria present in the water and can make a decision (or propose a course of action) whether or not to mitigate the bacteria. Because the water-going apparatus can include a location sub-system, such as GPS or a similar apparatus that provides the location of the water-going apparatus, one can provide the step of having the water-going apparatus traverse a region of a body of water, such as a lake, and report its location and a corresponding concentration of algae. In such a step, the water-going apparatus can map out an area or portion of the water-going body that is approaching the condition under which a HAB is likely to form, so that one can decide whether it is appropriate to begin a mitigation step so as to prevent a HAB from actually forming in the near future. In addition, the step of using an aerial observation sub-system such as a tethered drone with the ability to scan an area surrounding the location of the water-going apparatus can provide further information on the possible extent and/or the direction of motion of an incipient HAB. In addition, the use of additional optical sensors to monitor the concentration of algae in the effluent from the HAB mitigation step can be helpful in determining how effective the mitigation step has been, and can allow one to tailor the mitigation step so as to treat the algae present, but not to overtreat the water once the algae have been mitigated sufficiently.

The Advantages of Real-Time In Situ Testing

The data obtained using a real-time sensor is accurate at the time it is obtained and represents data that describes the condition of the water at the time of measurement. Using sensors that are commercially available, data can be obtained in real-time (less than one second per measurement). This provides many advantages, in particular relating to the time that data is obtained and to the accuracy of that data, over monitoring using methods that involve taking water samples, transporting them to a laboratory and testing in the laboratory.

A commercially available Phycocyanin Blue-Green Algae Sensor (BGA-PC) and a commercially available Phycoerythrin Blue-Green Algae Sensor (BGA-PE) are available from In-Situ Inc., 221 East Lincoln Avenue, Fort Collins, Colo. 80524 USA. According to the vendor, the data provided by the sensors can be retrieved wirelessly using software the vendor can provide. The sensors can operate when immersed in water.

Chlorophyll A is a specific form of chlorophyll used in oxygenic photosynthesis. It absorbs most energy from wavelengths of violet-blue and orange-red light, and it is a poor absorber of green and near-green portions of the spectrum.

One of the main distinctions between Chlorophyll A and B is in the color of the light that they absorb. Chlorophyll B absorbs blue light. Chlorophyll B's central role is to expand the absorption spectrum of organisms.

A commercially available CHLOROPHYLL A sensor is also available from the same vendor.

The sensors, which are described in U.S. Pat. Nos. 9,778, 180, 10,393,654 and 10,989,657, include an LED light source. According to the vendor, the sensors employ separate chlorophyll and blue-green algae sensors which can excite and detect a smaller range of the visible light spectrum than combined sensors in order to increase performance while minimizing interferences from other fluorescence sources. In addition, the vendor states that ambient light rejection blocks external light from affecting the sensor for more consistent monitoring and calibration across different sites. Therefore, it is believed that one should be able to use these sensors without regard to whether ambient light is present, which means that operation at any time (during daylight or at night, or for example, during 24 hour operation) is possible. Furthermore, the vendor states that the sensors use separate frequencies, providing a unique digital signature for each light source to minimize interference and improve accuracy. Therefore, it is believed that the use of multiple sensors to monitor specific areas in an array is possible because the data from each sensor can be identified by its individual digital signature.

Apparatus

The invention relates to the detection, assessment and mitigation of harmful water-borne bacteria such as cyanobacteria.

In general terms, the invention can be understood by recognizing that an apparatus is designed to traverse a body of water by means of a propulsion system. As the apparatus traverses the water, it collects and localizes water into a mitigation sub-system. As the water passes through the mitigation sub-system, it is exposed to at least one irradiation source. In some embodiments, the water is subjected to the addition of microbubbles. In some embodiments, the water is subjected to ultrasonic sound (sonication). The irradiation sources are localized so as to ensure optimal exposure of UV wavelengths to the collected water. A result from the irradiation sources is a disruption in the cellular processes of the microorganisms contained within the water. In some embodiments the water and its contents are exposed to ozone. Any excess ozone is converted to oxygen before the water is returned to the environment. As the water exits the mitigation sub-system, all specimens are returned to the same body of water from which they came. The system is not designed to extract or hold any material, other than samples for testing, nor does it emit any harmful chemicals into the water. The organisms collected by the apparatus are returned to the water with one very important feature; that the organisms (cyanobacterium) have now been exposed to a sufficient treatment so as to disrupt their cellular processes. The result is cell death. In one embodiment, the apparatus is designed to traverse a body of water, rather than bringing the water to the apparatus. This apparatus can be brought into an area as a preventative method, or to reduce the longevity of an already existing blue-green algae outbreak.

The invention provides systems and methods that render such cyanobacteria unable to replicate, for example by means of interfering with their DNA and RNA processes, without the expense and dangers associated with employing chemical methods.

In one embodiment, the present invention comprises an electromechanical device, designed to collect cyanobacterium from a water source, and to direct their movement in and about an irradiation source, whereby said cyanobacterium are subjected to concentrated irradiation, such as from a plurality of a UV (UV-A, UV-B, UV-C) light source. The collection system is designed to extract cyanobacterium from source water, and to neutralize the harmful bacteria, such as to interfere with the DNA and RNA processes involved in cellular functioning, thereby rendering the bacterium unable to sustain life and or the ability to replicate; all of which are subject to neutralization through the repeated exposure to an irradiation type light source.

In one embodiment, an apparatus that can provide useful real-time information about the condition of a water body as regards the presence (or absence) of BGA-PC, BGA-PE and Chlorophyll A includes sensors that can detect BGA-PC. BGA-PE and/or Chlorophyll A in bacteria in water, and a vessel that can carry the sensor or sensors on water, so that the sensors perform detection steps under control of an operator or a control device. The vessel includes a flotation device, a motor, a device that can measure the vessel location (such as a GPS sensor), a device that can treat a water sample in the apparatus, a device that can perform at least one of recording data, transmitting data and using the data to control further operations, the device that controls the sensors, and a device that can transmit data and can receive data and instructions for operation of the vessel and the detectors.

In describing the invention, it will be understood that a number of methods, techniques and steps are disclosed. Each of these has individual benefit and each can also be used in conjunction with one or more, or in some cases all, of the other disclosed methods, techniques and steps. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims. A more complete description of the operation of the various systems in the apparatus is given below in the section titled METHODS OF OPERATION.

FIG. 1 is a cross sectional diagram 100 in which are shown an irradiation chamber 102, a water level represented by dotted line 104, motors 106, 106', a deck 108, pontoons 110, 110' and a funnel-like water entry denoted by arrows 112.

FIG. 1 depicts the apparatus with an irradiation chamber, wherein cyanobacterium are collected and localized. The localization allows cyanobacterium to receive a lethal dose of UV light.

The apparatus of FIG. 1 is configured to traverse at or near the surface of the water where thermal stratification is likely to occur. The stratification causes the collection of cyanobacterium at or near a water's surface.

The apparatus of FIG. 1 is further comprised of propulsion devices to aid in the traversing through water.

The propulsion devices of FIG. 1 are configured as either electric or fuel assisted propulsion systems. In various embodiments, power may be supplied by batteries, by renewable energy sources, by fuel powered engines or by fuel powered electrical generators.

The apparatus of FIG. 1 is configured to include a deck or dry area configured to house control and navigation electronics.

Figure 2:
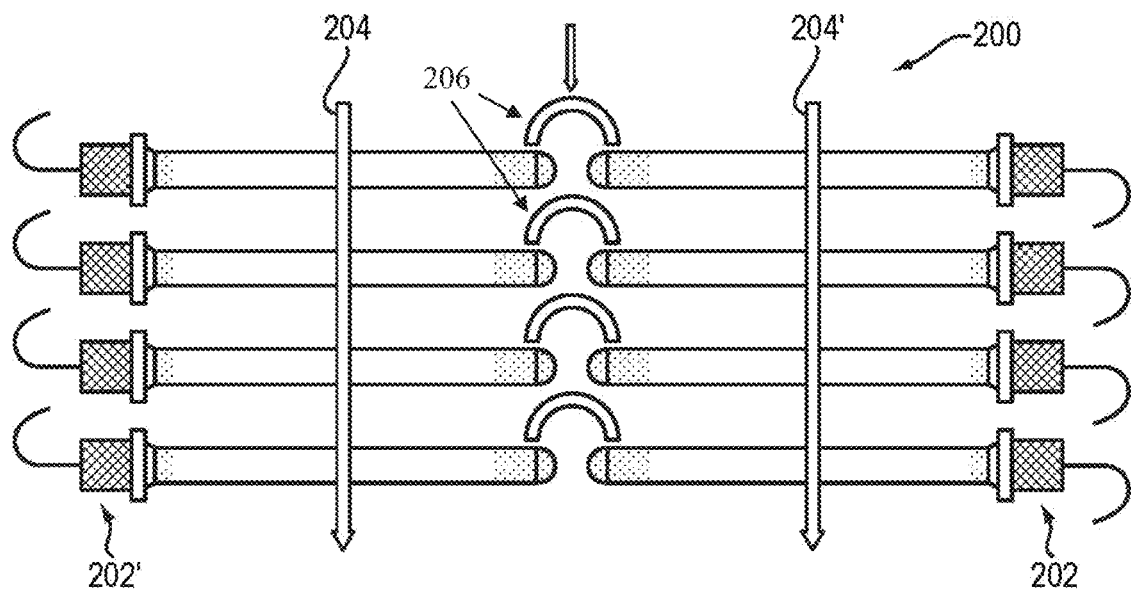
FIG. 2 depicts one configuration of the layout for the irradiation sources in which the irradiation sources are depicted in a horizontal position.

FIG. 2 is a plan view of the layout of an irradiation chamber 200 in which are located one or more irradiation sources 202, 202' and in which diagram is shown the direction of a water flow illustrated by arrows 204, 204'.

FIG. 2 depicts one configuration of the layout for the irradiation sources in which the irradiation sources are depicted in a horizontal position.

The irradiation sources of FIG. 2 can also be configured in a vertical position.

The irradiation sources of FIG. 2 are configured to receive directed water flow by means of employing baffles 206. The baffles 206 are configured to redirect water flow towards the irradiation sources to maximize irradiation exposure.

The irradiation sources of FIG. 2 are depicted in two rows of 16. The irradiation sources may include more or fewer irradiation sources. In some instances the terms "irradiation" and "illumination" are used interchangeably, but are intended to refer to light in one or more of the ultraviolet ranges of UV-A, UV-B, and UV-C, and/or to cavities in which such ultraviolet light may be applied to samples of interest.

The irradiation sources of FIG. 2 are designed to permit water to flow in and around the irradiation sources. The water is localized around the irradiation sources to ensure optimum exposure of UV sources.

Figure 3:
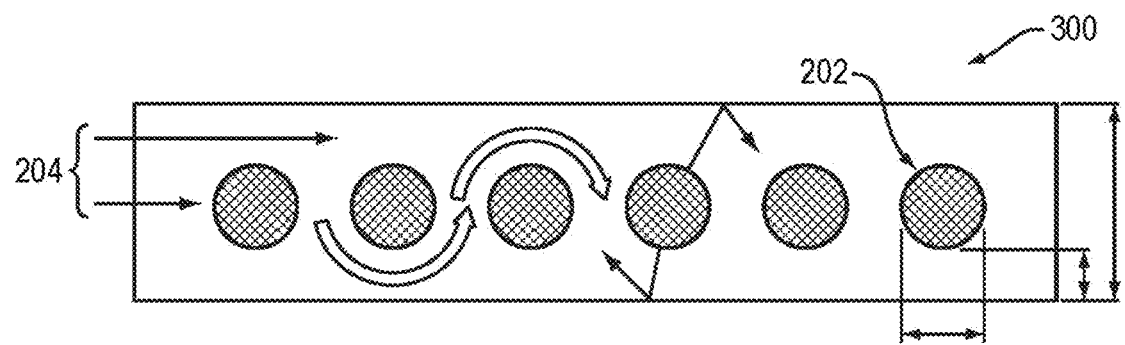
FIG. 3 depicts a cross section view of the irradiation sources configured in a horizontal position.

FIG. 3 is a cross section view 300 of the irradiation chamber 200, in in which are located one or more irradiation sources 202, 202' and in which diagram is shown the direction of a water flow illustrated by arrows 204, 204'.

FIG. 3 depicts a cross section view of the irradiation sources configured in a horizontal position.

The irradiation sources of FIG. 3 are configured to permit water flow in and around the irradiation sources. The flow is localized to ensure optimum exposure of UV sources.

As illustrated in FIG. 3 the localization of water in the irradiation chamber is used to control the intensity of irradiation that is applied to specimens of interest. The inverse square law states that as irradiation propagates to a distance twice a distance from its origin will spread out to 4 times the coverage area, resulting in $\frac{1}{4}^{th}$ the intensity.

Figure 4:
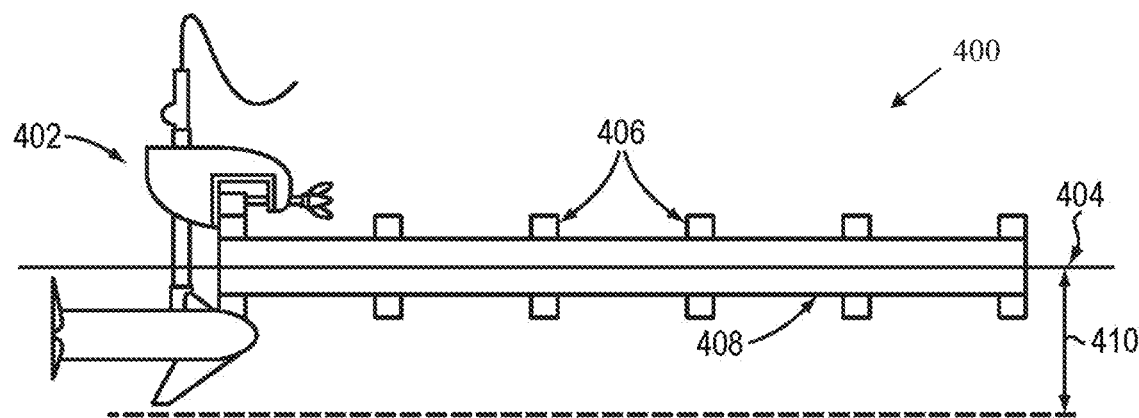
FIG. 4 schematic diagram in cross sectional view that depicts one embodiment for providing propulsion to the apparatus comprising a propulsion device located in the stern of the apparatus.

FIG. 4 is a schematic diagram 400 in cross sectional view illustrating the mounting of a motor 402 in which is illustrated a water level 404, a cage or support 406 for an illumination chamber 408, and a distance 410 representing a clearance distance to allow the motor 402 to operate without encountering obstacles.

FIG. 4 depicts one configuration for providing propulsion to the apparatus comprising a propulsion device located in the stern of the apparatus.

The of apparatus of FIG. 4 further comprises of external supports for the irradiation chamber. The supports of FIG. 4 are designed to prevent flexing of the irradiation chamber from pressures acting on its external surfaces. The pressures acting on its surfaces include buoyancy and momentum factors.

Figure 5:
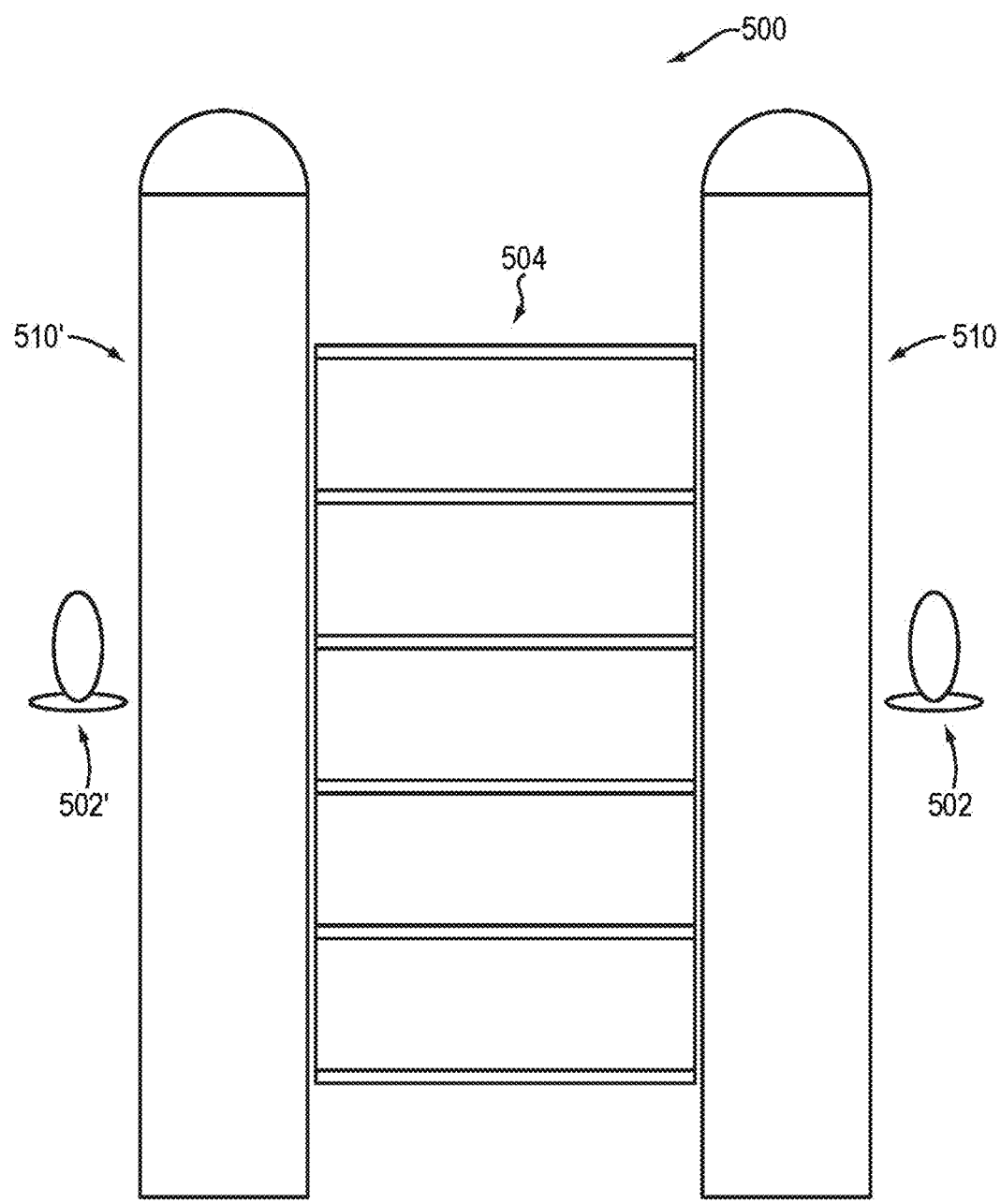
FIG. 5 is a schematic diagram in plan view that depicts a second location of a propulsion systems.

FIG. 5 is a schematic diagram 500 in plan view in which are illustrated pontoons 510, 510' to which are attached motors 502, 502' and which pontoons support an illumination chamber 504.

FIG. 5 depicts a second location of propulsion systems. The revision serves to aid in navigation, as well as a reduction in applied forces necessary to steer the device through the water. Furthermore, the revision of FIG. 5 helps to balance the weight of the propulsion systems on the device.

Figure 6A:
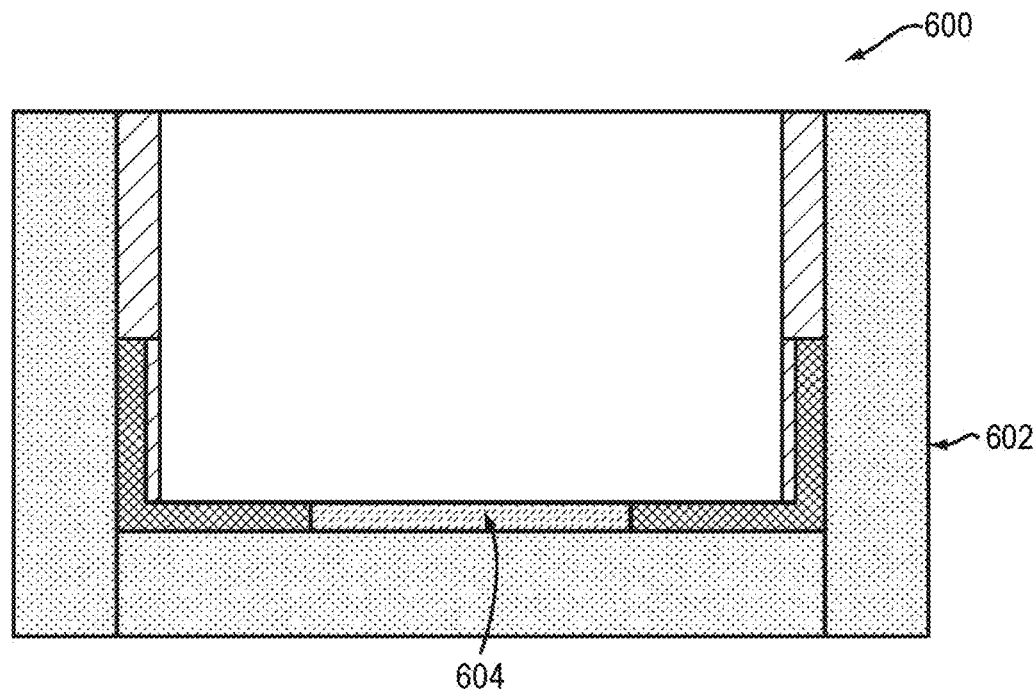
FIG. 6A is a schematic diagram in cross sectional view that depicts a cross section of external supports to the irradiation chamber.

FIG. 6A is a schematic diagram 600 in cross sectional view illustrating a support structure 602 that is configured to contain an illumination chamber 604.

FIG. 6A depicts a cross section of external supports to the irradiation chamber. The supports are comprised of angular and tubular supports, in both horizontal and vertical configurations. The supports encapsulate the irradiation chamber.

The external supports of FIG. 6A are further comprised of foam. The foam of FIG. 6A is configured to provide a separation between the irradiation chamber and the external supports. The foam provides both a flexible lining to absorb vibration, as well as to reduce friction between the irradiation chamber and the external supports.

The external supports of FIG. 6A are configured as a cage. The cage is configured to encapsulate, or to provide support for the irradiation chamber.

The external supports of FIG. 6A are configured to be removable. The external top supports of FIG. 6A are configured to be removable to provide access to the irradiation chamber.

Figure 6B:
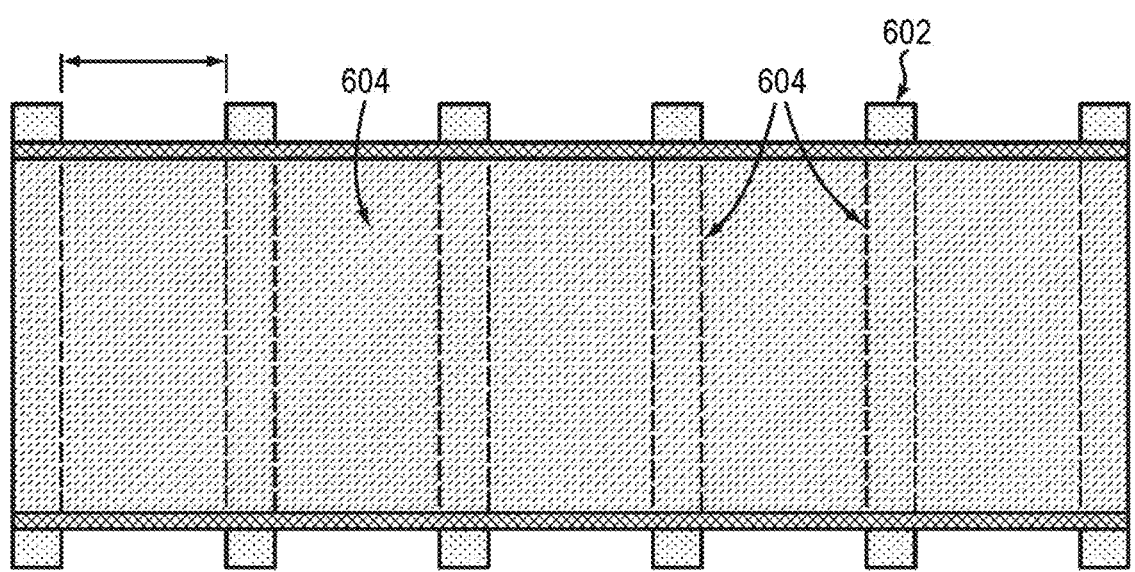
FIG. 6B is a is a schematic diagram in plan view of the irradiation chamber.

FIG. 6B is a is a schematic diagram 620 in plan view illustrating a plurality of support structures 602 that are configured to contain an illumination chamber 604.

Figure 7:
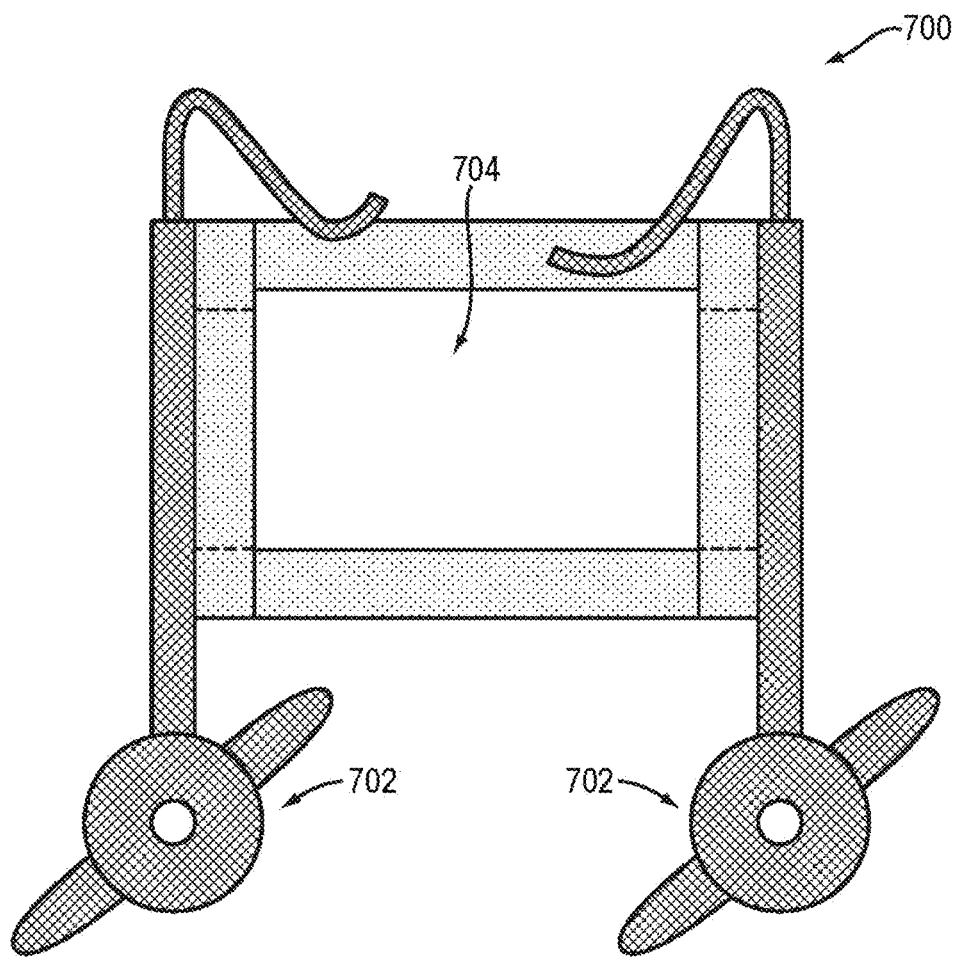
FIG. 7 is a schematic diagram that depicts the propulsion systems configured to be clamped to the device, particularly by being thru-bolted to external supports.

FIG. 7 is a schematic diagram 700 in which are illustrated motors 702 attached to an illumination chamber 704. By driving each of the motors separately, the apparatus can be steered in the water.

FIG. 7 depicts the propulsion systems configured to be clamped to the device, particularly by being thru-bolted to external supports of FIG. 6A.

The propulsion systems of FIG. 7 are configured to be controlled via electrical communication cables. The communication cables are in electrical communication with a control module.

Figure 8:
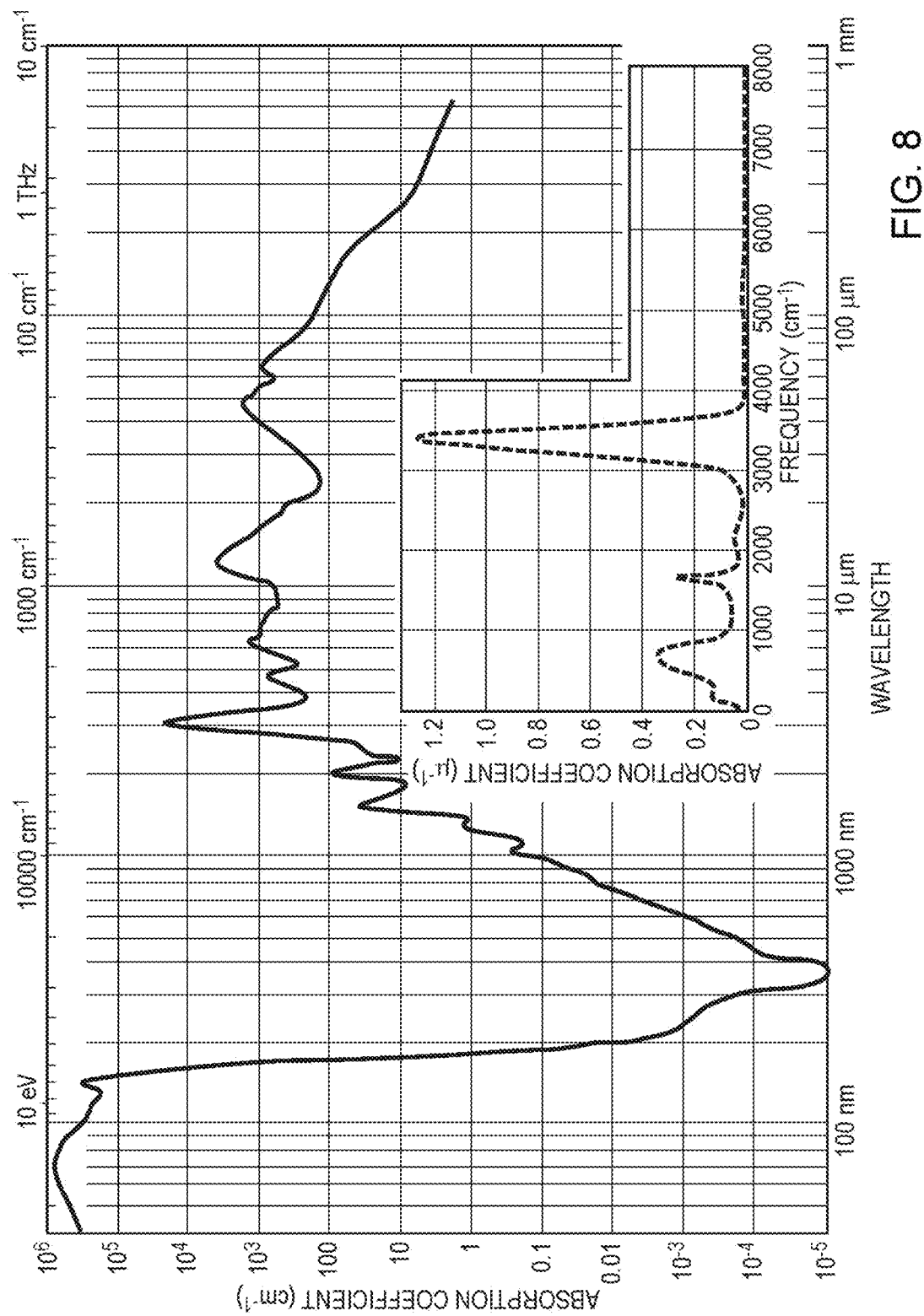
FIG. 8 depicts the electromagnetic spectrum comprising the UV spectrum along with a curve illustrating the absorption coefficient of illumination in water.

FIG. 8 depicts the electromagnetic spectrum comprising the UV spectrum along with a curve illustrating the absorption coefficient of illumination in water. The wavelength of UV radiation (UVR) lies in the range of 100-400 nm and is further subdivided into UV-A (315-400 nm), UV-B (280-315 nm), and UV-C (100-280 nm). The UV component of terrestrial radiation from the midday sun comprises about 95% UV-A and 5% UV-B; UV-C and most of UV-B are removed from extraterrestrial radiation by stratospheric ozone.

The optimal germicidal UV wavelength of UV-C is situated at approximately 264 nm.

Figure 9:
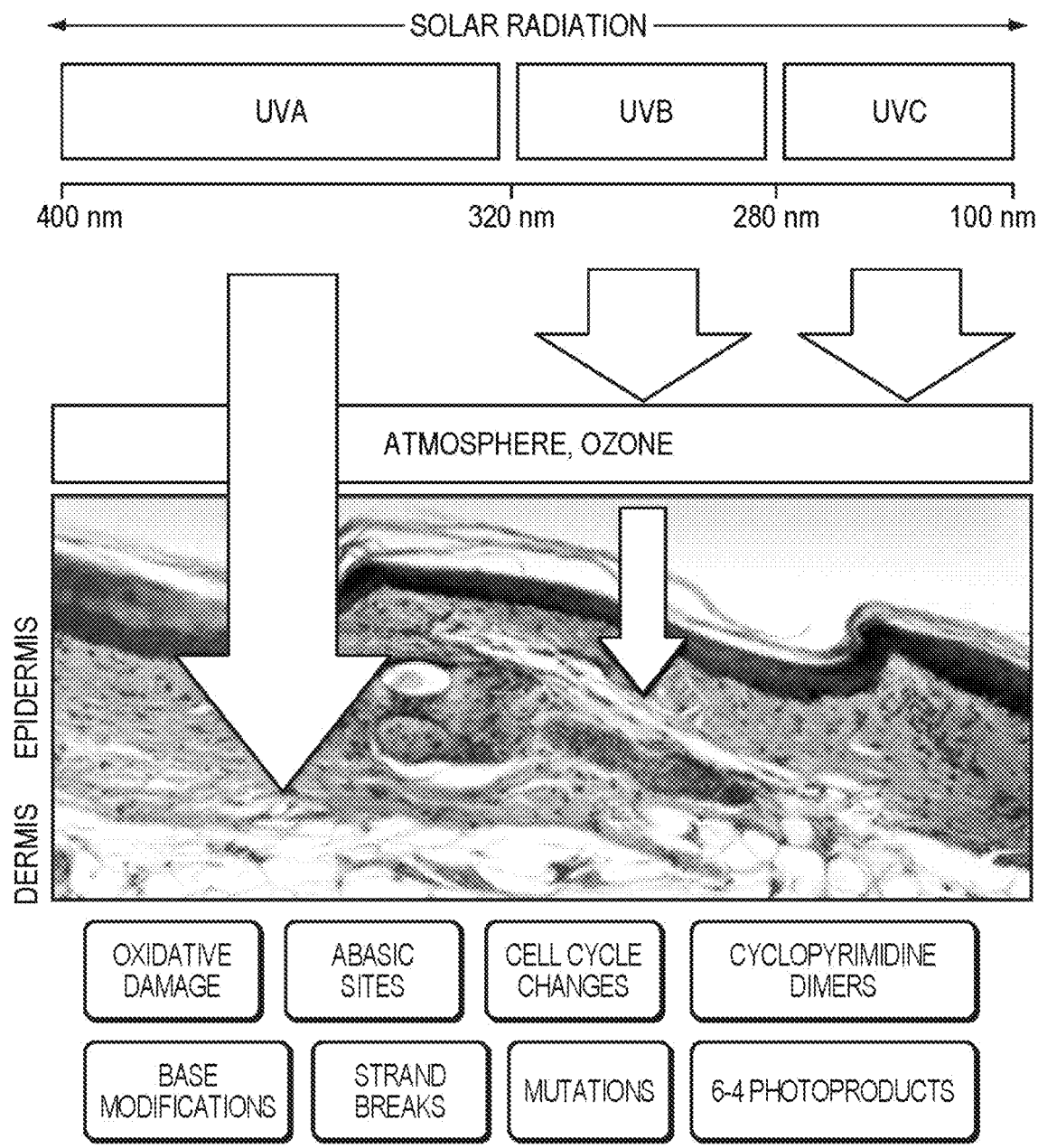
FIG. 9 schematically illustrates the impact of varying UV wavelengths (UV-A, UV-B, and UV-C) on the biological processes of cells.

FIG. 9 schematically illustrates the impact of varying UV wavelengths (UV-A, UV-B, and UV-C) on the biological processes of cells.

FIG. 9 describes how exposure to UV-A light can affect the health of cells by generating oxidative damage and strand breaks in DNA.

FIG. 9 describes how exposure to UV-B light can affect the health of cells by generating cell cycle changes and mutations in cellular processes.

FIG. 9 describes how exposure to UV-C light can affect the health of cells by generating cyclo pyrimidine dimers (lesions) in cells.

Figure 10:
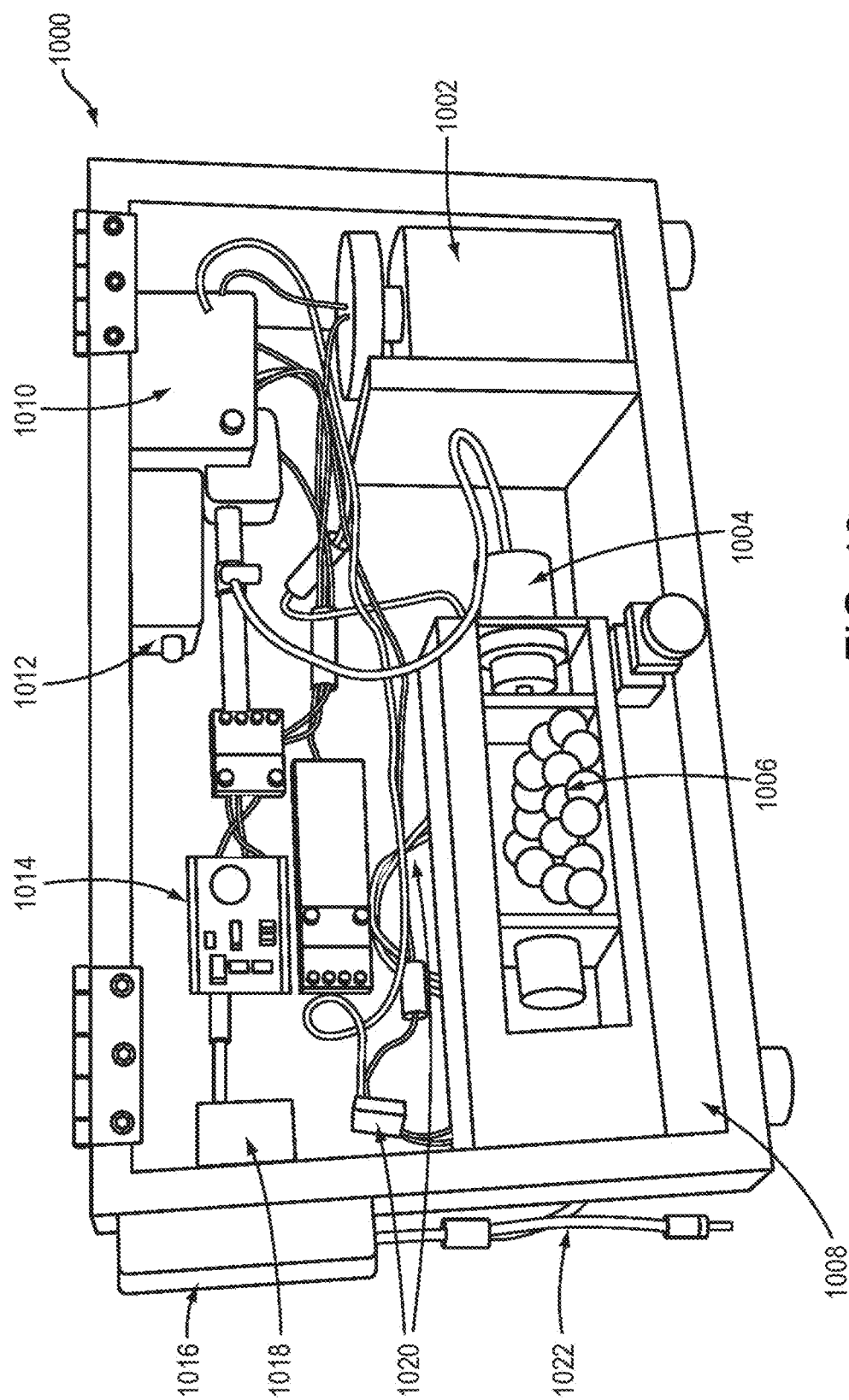
FIG. 10 is an illustration of a benchtop prototype apparatus useful for mitigating cyanobacteria.

FIG. 10 is an image of a benchtop prototype apparatus 1000 useful for mitigating cyanobacteria. In FIG. 10, there are illustrated a containment/storage vessel 1002, a UV-C lamp 1004, an optical chamber 1006 built from acrylic exterior blocks which prevent 98% of UV-C from escaping, an acrylic safety window 1008 that permits visual observation during the operation of the apparatus, a UV-C lamp ballast 1010, multi-colored LED safety indicators 1012 (red, yellow, green), an Arduino UNO microcontroller unit 1014, a 4-watt variable air supply 1016, an ultrasonic generator 28 kHz @ 0.75-watt 1018, direct electrical communication between the ultrasonic generator and transducers 1020 and an air line with directional valve 1022.

The Arduino Uno is an open-source microcontroller board based on the Microchip ATmega328P microcontroller and developed by Arduino.cc. The board is equipped with sets of digital and analog input/output (I/O) pins that may be interfaced to various expansion boards (shields) and other circuits. The board has 14 digital I/O pins (six capable of PWM output), 6 analog I/O pins, and is programmable with the Arduino IDE (Integrated Development Environment), via a type B USB cable. It can be powered by the USB cable or by an external 9-volt battery, though it accepts voltages between 7 and 20 volts. It is similar to the Arduino Nano and Leonardo. The hardware reference design is distributed under a Creative Commons Attribution Share-Alike 2.5 license and is available on the Arduino website. Layout and production files for some versions of the hardware are also available. Arduino products may be purchased from various venders such as Newark, 300 S. Riverside Plaza, Suite 2200, Chicago, Ill. 60606.

Operation of the apparatus illustrated in FIG. 10 is now described, and results obtained are illustrated in Table I below. The cyanobacteria are loaded into the optical chamber. The chamber consists of optical mirrors (97% reflectivity) and has a Rexim 6-watt UV-C lamp (Quartz sleeved 254 nm UV output @ 1 cm=5000 µw/cm$^2$) configured horizontally through the chamber. The sequence is controlled via microprocessor control, which is activated only when the indicator LED displays green. The sequence is initiated via external laptop in electrical communication with the Arduino via a USB. Once initiated, the program activates a combination of UV-C, air injection (Zhongle nanobubble generating ceramic air stone Model #ASC-89204), and Kemo ultrasound generator (Model #M048N, operating at 12-15 VDC @<50 mA) via a relay switch. Power is derived from a ballast, which is in electrical communication with line voltage source. Light escaping the chamber is blocked (98%) by its exterior acrylic, which is further enhanced by an additional acrylic window which adds an additional 98% of blockage. Upon completion of the sequence, the LED changes from red to green, indicating that it is safe to remove the sample. This benchtop utilizes UV-C, air, and ultrasound sources alone or in combination for mitigation of cyanobacteria. It is believed that each of the UV-C illumination, microbubbles of air and ultrasonic energy, alone or in combination, can mitigate the cyanobacteria.

TABLE I

Experimental Results

| UV-C dose | Microbubble addition | Sonication Intensity/ frequency | Observation Period | Net Reduction |
|---|---|---|---|---|
| 24 watt-seconds | | | 24 hours | −59.2% |
| 36 watt-seconds | | | 24 hours | −78.8% |
| 36 watt-seconds | yes | | 24 hours | −80.4% |
| 48 watt-seconds | yes | 6 watt-seconds/ 28 kHz | 24 hours | −96.5% |
| 48 watt-seconds | yes | 6 watt-seconds/ 28 kHz | 72 hours | −78% |

Figure 11:
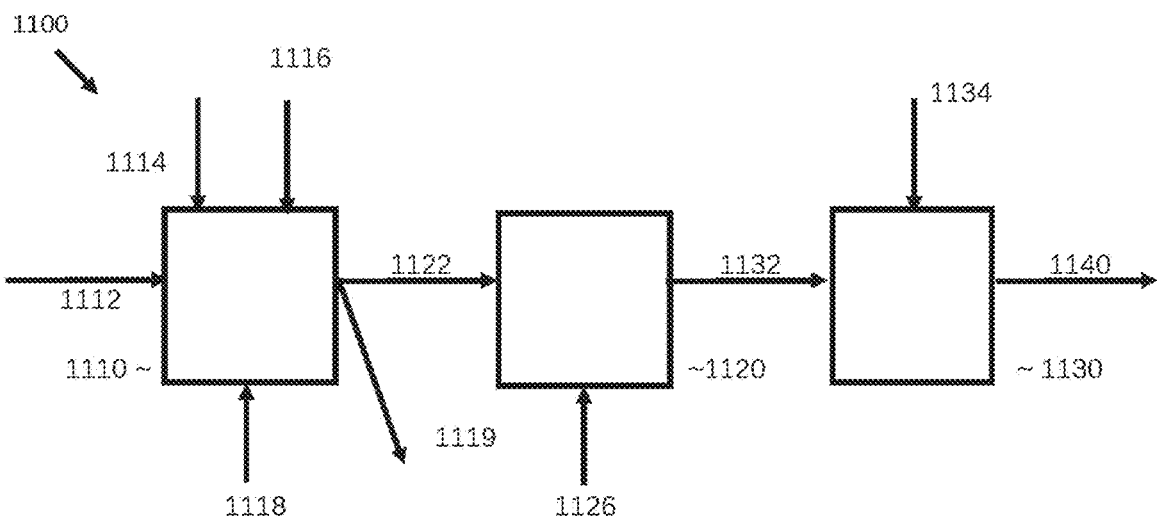
FIG. 11 is a schematic flow diagram of a first embodiment of a mitigation sub-system that uses ozone as a reagent.
Figure 13:
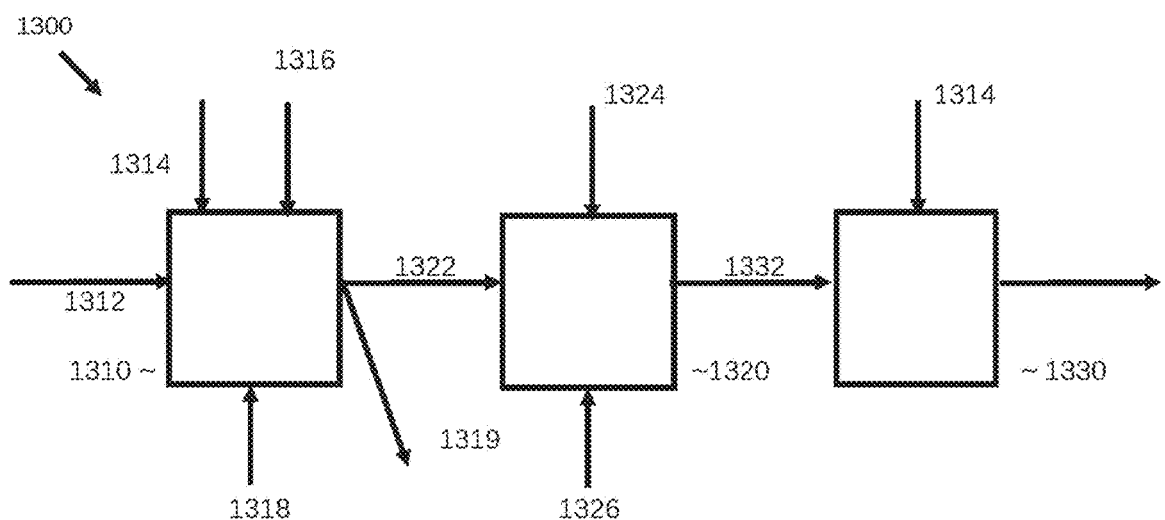
FIG. 13 is a schematic flow diagram of a second embodiment of a mitigation sub-system that uses ozone as a reagent.
Figure 12A:
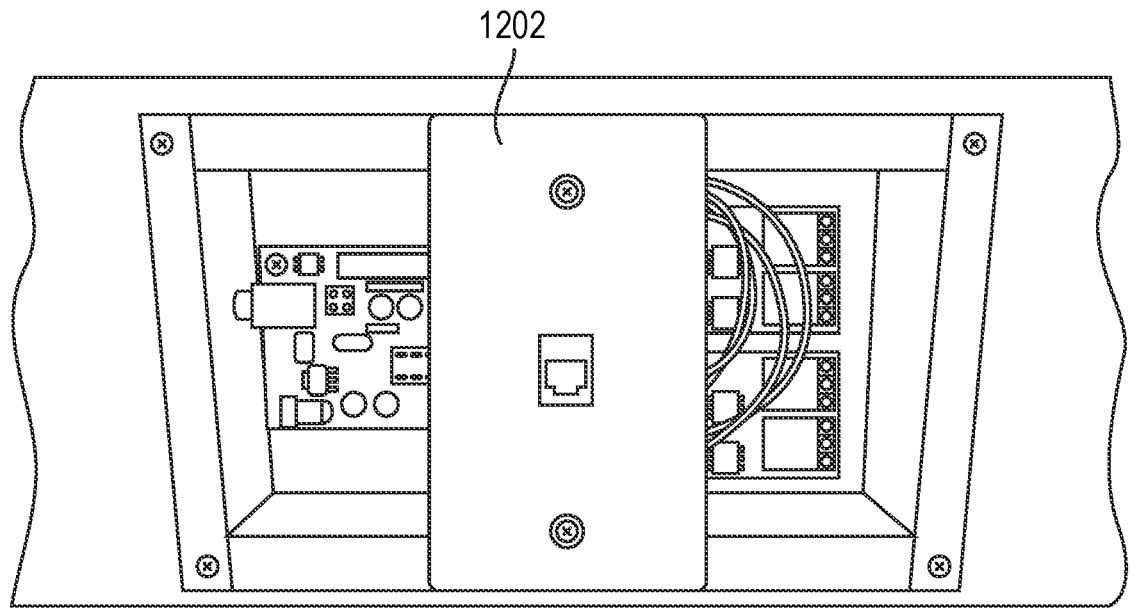
FIG. 12A to FIG. 12D are images of an embodiment of a benchtop prototype ozone generation apparatus that uses 185 nm UV illumination configured convert oxygen to provide ozone as a reagent.
Figure 12B:
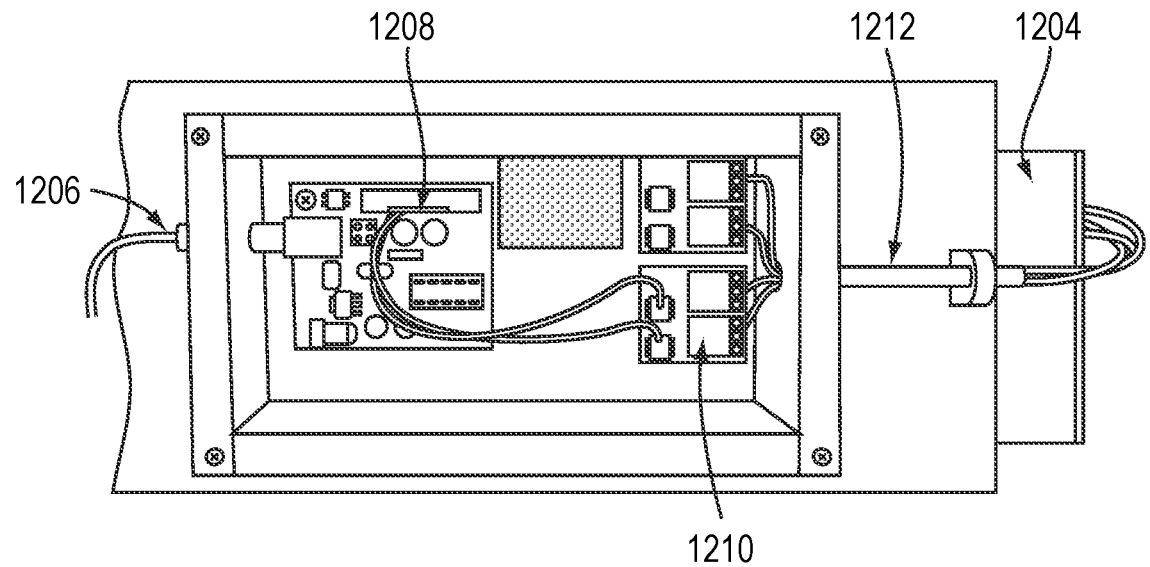
Figure 12C:
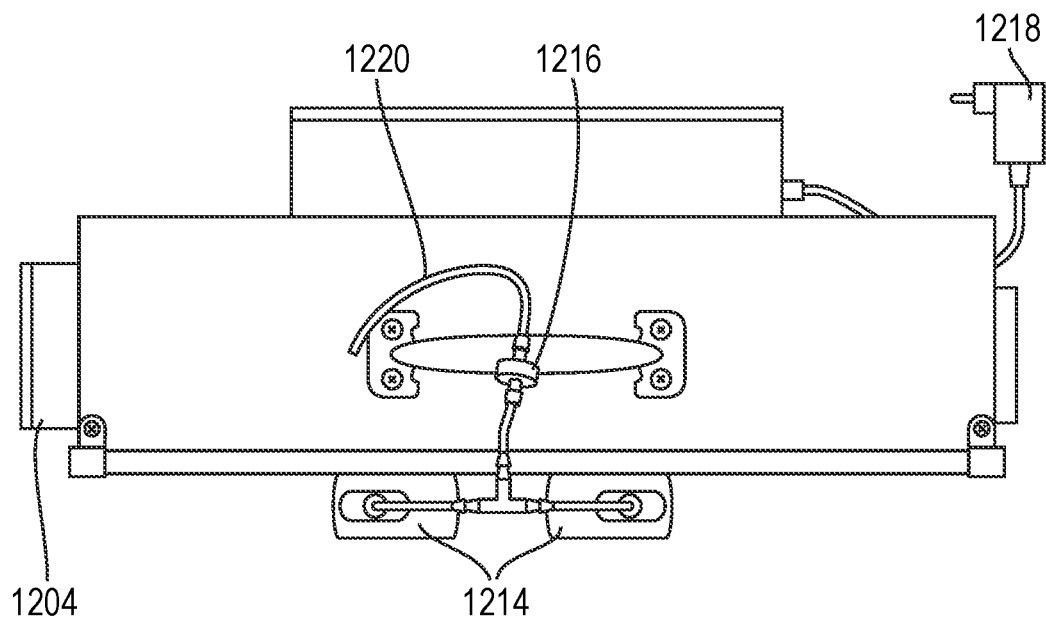
Figure 12D:
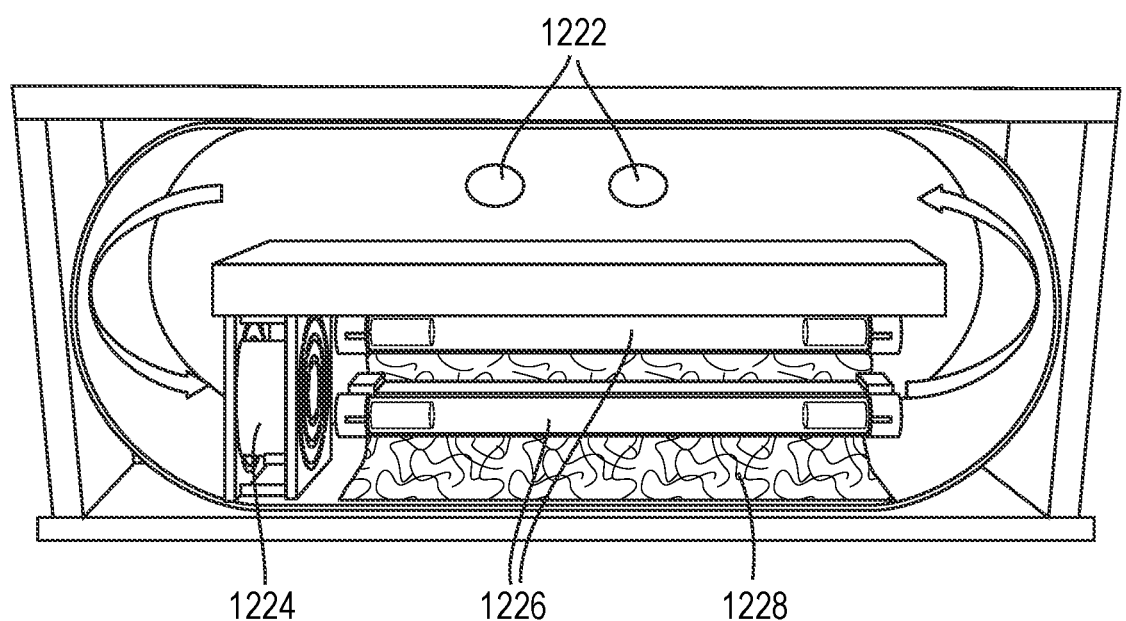

In alternative embodiments, the optical chamber 1006 of FIG. 10 in which cyanobacteria in water are treated can be replaced with the embodiments illustrated in FIG. 11 or in FIG. 13.

FIG. 11 is a schematic flow diagram 1100 of a first embodiment of a mitigation sub-system that uses ozone as a reagent. In FIG. 11 there are three reaction zones, illustrated as separate structures 1110, 1120 and 1130. It is to be understood that the processes that occur in each zone are isolated from the processes that occur in a different zone, whether by having discrete reaction units or cells or simply by having the three reaction regimes separated by suitable distance in a flow system. As illustrated schematically in FIG. 11 water containing cyanobacteria that are to be rendered harmless flow into reaction zone 1110 as indicated by arrow 1112. When in reaction zone 1110 the water containing the cyanobacteria is subjected to one or more of UV-C illumination (e.g., 254 nm illumination) 1114, sonication 1116 and a gas containing oxygen ($O_2$) 1118 introduced by way of a ceramic air stone so as to create a plurality of microbubbles in the water. After treatment in reaction zone 1110, the water is conveyed as illustrated schematically by arrow 1122 to reaction zone 1120. Optionally, the water may be filtered to remove solids (illuminated cyanobacteria, which are rendered harmless) as illustrated by arrow 1119. In reaction zone 1120 there is applied gas containing ozone ($O_3$) 1126 by way of a ceramic air stone so as to create a plurality of microbubbles in the water. The gas containing ozone may be provided from a source in which ozone is present. Well known ozone sources include reactors in which air or other oxygen-bearing gas is subjected to electric discharge or to UV illumination having a wavelength of 185 nm. The gas containing ozone may be provided by use of a pump in some embodiments. It is believed that the ozone reacts with both the cyanobacteria that may be present and with harmful chemicals produced by the cyanobacteria. The water in reaction zone 1120 is then transferred to reaction zone 1130 as illustrated by arrow 1132. In reaction zone 1130 the water is subjected to UV illumination 1134 containing the wavelength of 254 nm which is believed to convert the remnant of the ozone ($O_3$) to oxygen ($O_2$) so that effluent exiting the reaction zone 1130, which exiting effluent travels as illustrated schematically by way arrow 1140, does not contain ozone which is harmful to the environment.

In one embodiment, we have generated ozone in situ using 185 nm lamps with recirculating air being forced past the lamps repeatedly, so that the amount of ozone generated is increased in each pass. The ozone is then pumped into the reaction zone 1120 where it interacts with the cyanobacteria before moving to reaction zone 1130 where it is passed through a series of 254 nm UVC lamps which act as a filtering mechanism to break up the ozone. This reduces the amount of dissolved ozone released into the environment. Ozone will naturally decay is 30-60 minutes. However, if released into the environment, it will react with organisms in the water until it does break down. This is why breaking it down artificially is important.

FIG. 12A to FIG. 12D are images of an embodiment of a benchtop prototype ozone generation apparatus that uses 185 nm UV illumination configured convert oxygen to provide ozone as a reagent. In FIG. 12A to FIG. 12D there are shown the following components: RJ45 Communications port 1202, 120 Volt AC power supply 1204, USB cable 1206, Arduino UNO 1208, relay modules 1210, power supply harness 1212, air pumps 1214, 1-way air valve 1216, low voltage supply 1218, exhaust port 1220, 12 vol DC fan 1224, 185 nm UV lamps 1226 and reflective aluminum 1228.

FIG. 13 is a schematic flow diagram of a second embodiment of a mitigation sub-system that uses ozone as a reagent. In FIG. 13 there are three reaction zones, illustrated as separate structures 1310, 1320 and 1330. It is to be understood that the processes that occur in each zone are isolated from the processes that occur in a different zone, whether by having discrete reaction units or cells or simply by having the three reaction regimes separated by suitable distance in a flow system. As illustrated schematically in FIG. 13 water containing cyanobacteria that are to be rendered harmless flow into reaction zone 1310 as indicated by arrow 1312. When in reaction zone 1310 the water containing the cyanobacteria is subjected to one or more of UV-C illumination (e.g., 254 nm illumination) 1314, sonication 1316 and a gas containing oxygen ($O_2$) 1318 introduced by way of a ceramic air stone so as to create a plurality of microbubbles in the water. After treatment in reaction zone 1310, the water is conveyed as illustrated schematically by arrow 1322 to reaction zone 1320. Optionally, the water may be filtered to remove solids (illuminated cyanobacteria, which are rendered harmless) as illustrated by arrow 1319. In reaction zone 1320 there is applied gas containing oxygen ($O_2$) 1326 way of a ceramic air stone so as to create a plurality of microbubbles in the water. Alternatively, or in addition, the gas containing oxygen (which may be air) may be reacted by application of UV illumination 1324 having a wavelength of 185 nm to convert some of the oxygen to ozone ($O_3$) in situ. The gas containing oxygen may be provided by use of a pump in some embodiments. It is believed that the ozone reacts with both the cyanobacteria that may be present and with harmful chemicals produced by the cyanobacteria. The water in reaction zone 1320 is then transferred to reaction zone 1330 as illustrated by arrow 1332. In reaction zone 1330 the water is subjected to UV illumination 1334 containing the wavelength of 254 nm which is believed to convert the remnant of the ozone ($O_3$) to oxygen ($O_2$) so that effluent exiting the reaction zone 1330, which exiting effluent travels as illustrated schematically by way arrow 1340, does not contain ozone which is harmful to the environment.

Using real-time sensors, it is possible to repeatedly measure desired values of BGA-PC, BGA-PE and Chlorophyll A at the same location over time, for example at multiple times during a day, so that the amount of the algae of interest can be analyzed over time and location, so as to allow a projection of locations where a bloom of a BGA may be expected to occur.

Because such projections can be made beginning at a very low concentration value of a BGA of interest, it can be possible to intervene to reduce the concentration of the BGA before it reaches a hazardous value. Systems that require sampling, transport to a laboratory, and analysis off-site cannot provide accurate information that compares to what can be obtained by the apparatus and its method of use described herein.

Figure 14:
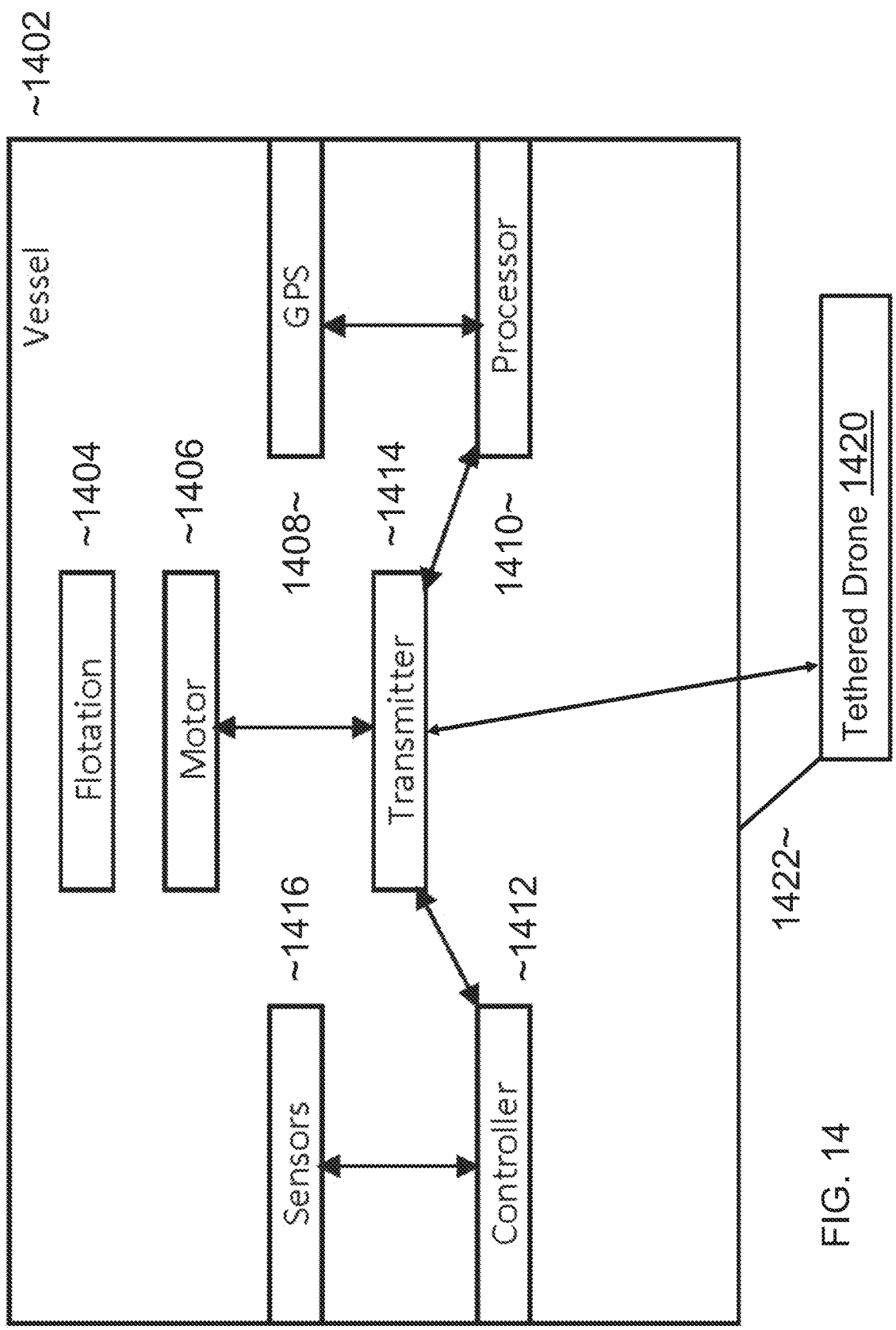
FIG. 14 is a schematic diagram of one embodiment of the apparatus.

FIG. 14 is a schematic diagram of one embodiment of the apparatus. In FIG. 14 there is illustrated a vessel 1402 that includes a flotation sub-system 1404, a propulsion sub-system 1406, a location sub-system 1408 that can measure the vessel location (such as a GPS sensor), a microprocessor-based device 1410 that can perform at least one of processing data, recording data, transmitting data and using the data to control further operations including providing an assessment sub-system for determining the concentration of algae in water relative to a predetermined reference concentration, a control sub-system 1412 operating on the microprocessor-based device 1410, a communications sub-system 1414 such as a transmitter/receiver that can transmit data and can receive data and the instructions for operation of the vessel, an aqueous monitoring sub-system 1416 for monitoring the concentration of algae in water, a mitigation sub-system 1418, and an aerial observation sub-system 1420 (such as a tethered drone or a floating balloon that has a camera) connected to the vessel 1402 by a tether 1422. The control sub-system 1412 can control the vessel 1402, the flotation system 1404, the propulsion sub-system 1406, the location sub-system 1408, the microprocessor-based device 1410, the transmitter/receiver 1414, the aqueous monitoring sub-system 1416, the mitigation sub-system 1418 (which in various embodiments can be the sub-systems described and illustrated in FIG. 11 or alternatively in FIG. 13) and the aerial observation sub-system 1420. In other embodiments, control of any of the aforementioned devices can be performed by a human operator who is present on the vessel 1402, or who is remote from the vessel 1402, for example in a remote location on land.

The vessel 1402 is configured to monitor water conditions using aqueous monitoring sub-system 1416 for monitoring the concentration of algae in water. To aid in identifying areas of concern beyond the immediate vicinity (e.g., within line-of-sight), a aerial observation sub-system 1420 such as a tethered drone can be flown above the vessel 1402. The tethered drone is comprised of a control base which controls the length and tension of the tether 1422, as well as the drone 1420, typically a multi-rotor aircraft. Tethered drones 1420 receive power through the tether 1422, which allows the drone to stay in the air for extended period of times. Tethered drones do not require a part 107 FCC license so long as they remain under 150-foot ceiling. If areas of concern are spotted by a camera in the drone the vessel can be sent to the area. The tethered drone 1420 can be configured to have either RGB, spectral, or hyperspectral imagers to aid in identifying concentrations of cyanobacteria. Once the vessel has reached an area of interest identified by the tethered drone 1420, the aqueous monitoring sub-system 1416 can confirm the presence of blue green algae.

Figure 15A:
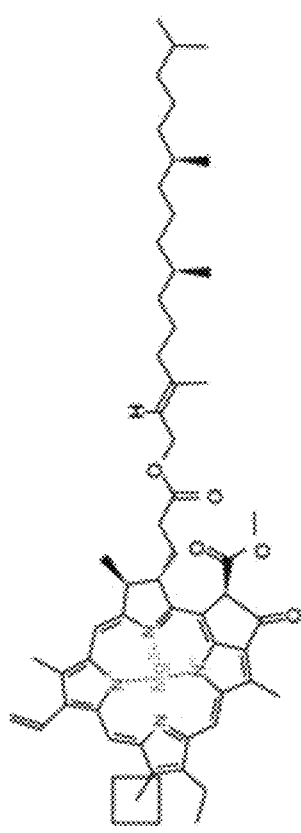
FIG. 15A is the structural representation of the chemical formula of Chlorophyll A.

FIG. 15A is the structural representation of the chemical formula of Chlorophyll A.

Figure 15B:
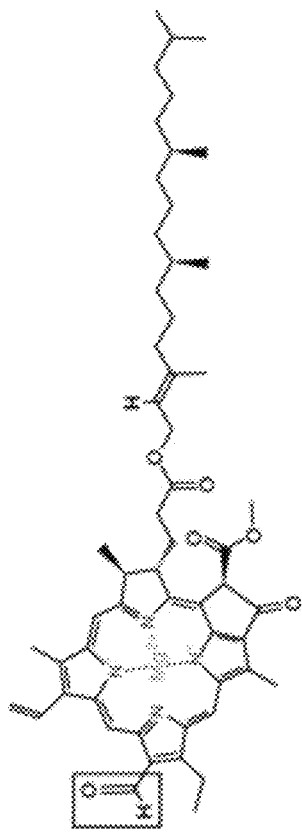
FIG. 15B is the structural representation of the chemical formula of Chlorophyll B.

FIG. 15B is the structural representation of the chemical formula of Chlorophyll B.

Figure 15C:
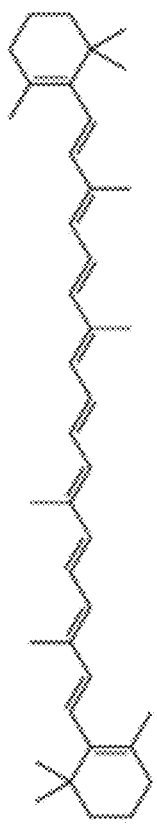
FIG. 15C is the structural representation of the chemical formula of p-carotene.

FIG. 15C is the structural representation of the chemical formula of β-carotene.

Figure 15D:
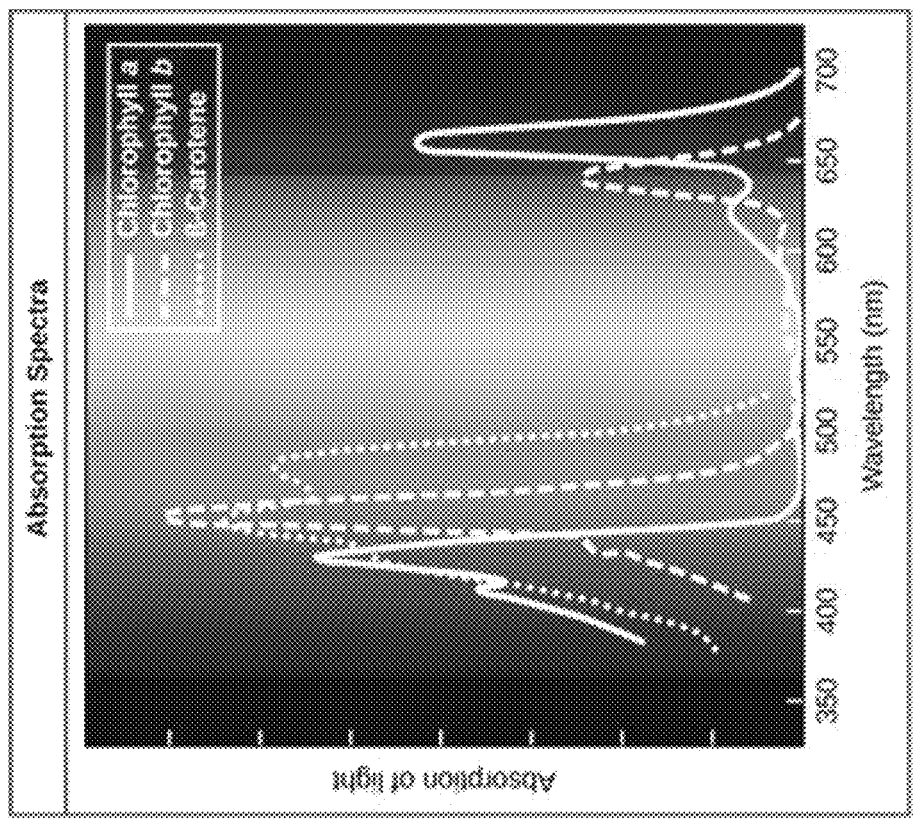
FIG. 15D is a diagram of the absorbance spectra of Chlorophyll A, Chlorophyll B and β-carotene.

FIG. 15D is a diagram of the absorbance spectra of Chlorophyll A, Chlorophyll B and β-carotene.

Methods of Operation

In one embodiment, the apparatus can be used as follows: The vessel can be driven over water in a region or area to be monitored for BGA. By way of example, the vessel maybe driven in a pattern similar to the pattern used to mow lawns, such as being driven in a first traverse for a given distance in a straight line, then turned about and driven in the opposite direction (parallel to and laterally offset from the first traverse) for a similar distance at an offset of a desired distance measured perpendicularly from the first traverse. As needed, the pattern of offset and traverse can be repeated for as many passes (traverses) as required to monitor a desired area. In some embodiments, a similar traverse pattern can be used in treating and mitigating algae.

During each traverse, the sensors in the aqueous monitoring sub-system measure the local concentration of BGA and associated water chemistry, the location of the measurements is recorded using the GPS, the data are recorded, that data may be transmitted and/or analyzed, and the operation and any instructions that an operator wishes to communicate to the vessel may be received. The controller acts to control the sensors as needed, to control the recording, analyzing and transmission of data as needed, and the operation of the vessel. The data can be collected in real-time, that is, essentially as fast as the sensors can measure the data (which is less than one second).

An operator (for example, a human operator) can instruct the vessel to travel to a location of interest, and to operate at that location to monitor BGAs and water quality.

There are three embodiments which are incorporated within the irradiation chamber and they include the following.

1. Nanobubbles which act as a harassing agent to transport bacteria towards the UV-C light because of a change in their buoyancy. In some embodiments, the nanobubbles can comprise ozone. As illustrated in FIG. 11 the ozone can be provided from a source of ozone. As illustrated in FIG. 13 the ozone can be generated within the mitigation sub-system (e.g., generated in situ).
2. UV-C irradiance which kills and or disrupts the cellular functioning of cyanobacteria by corrupting their DNA
3. Ultrasonic transducers operating at above 20 kHz break up internal gas vesicles or other structures within the cyanobacteria.

The irradiance chamber is designed to adjust its elevation in a body of water to optimize the localization of cyanobacteria. In some embodiments, as the cyanobacteria pass through the system, they can be bombarded with a cloud of nanobubbles. These bubbles are designed to attach to the surface of the cell membranes resulting in a change in their buoyancy or to provide a lifting action. This change in buoyancy generates a lifting action that causes an ascent of the cyanobacteria towards the UV-C sources. Theoretically it would be possible for the bacteria to flow through the system unharassed in the absence of a harassing agent. In the case of the irradiance chamber the nanobubbles become an agent that prevent the bacteria from flowing through the chamber with a reduced exposure to the UV-C sources. As the bacteria ascend they become proximate to the UV-C sources. This results in enhanced exposure to the UV-C source. For example, by bringing the bacteria closer to the surface of the water, there is less water through which the UV-C illumination (or equivalently, UV-C radiation) has to pass. As may be seen from the visible and UV spectra of liquid water shown in in FIG. 10, the absorption coefficient of water in the range of 100-200 nm rises steeply, so foreshortening the distance that the UV-C has to travel in the water effectively allows a higher total intensity of UV-C (for the same source intensity) to reach the bacteria.

In some embodiments, the UV-C light is the primary source of disruption of cyanobacteria. In various embodiments, UV-C light, nanobubbles comprising ozone and ultrasonic sound provided by ultrasonic transducers may be used individually or in combination to mitigate cyanobacteria.

The ultrasonic transducers can be used alone or as an augmentation system to the UV-C lamps. Sound travels quite nicely through water regardless of its turbidity. If there is a significant change in the turbidity of the water, the use of ultrasonic frequencies has been added to enhance the mitigation of cyanobacteria in response to those changes in turbidity. The ultrasonic transducers are designed to emit high frequency sound designed to penetrate the cell membranes of the cyanobacteria. This passthrough action allows the mitigation of the cells by inducing cellular changes because of the use of high frequency vibrations. These ultrasonic vibrations are designed to disrupt the air vesicles within the cyanobacteria which they utilize to manipulate their buoyancy in the water. The ultrasonic vibrations may also disrupt cyanobacteria by interaction with microbubbles on the surface of the cyanobacteria. Under normal operation the cyanobacteria manipulate their buoyancy to position themselves in favorable elevations within the water column to enhance their sunlight exposure. These cyanobacteria utilize photosynthesis to generate food so an absence of photosynthetic behavior would reduce their ability to survive.

In other embodiments, the ultrasonic excitation can also disrupt the cyanobacteria by disrupting the microbubbles on the surface of the cyanobacteria, which can cause the cell membrane of the cyanobacteria to be disrupted, thereby damaging, or destroying, the cyanobacterium itself.

Cyanobacteria left alone may be able to remain low within the chamber which would limit their exposure to the UV-C.

Experimental Results

Algae

Mitigation experiments were conducted on a number of freshwater lakes in New York. One experiment was performed at Lake Neatahwanta in Fulton, N.Y. The ozone concentration used was 5 ppm (5 parts per million). It was observed that this experiment reduced cyanobacterial chlorophyll by approximately 60%.

Another experiment was performed at Oneida Lake in Bridgeport, N.Y. The ozone concentration used was 10 ppm (10 parts per million). It was observed that this experiment reduced cyanobacterial chlorophyll by approximately 69.7%.

These reductions were based upon a comparison between pre and post treatment samples taken while the boat was in motion. Mitigation using UV-C with ozone resulted in the most photosynthetic stress out of all methods tested. Cells will not grow and thrive under these conditions, which explains the steady decline over several days.

The experimental data was observed using a mitigation threshold value of 36 watt-seconds of UV-C energy can reduce chlorophyll activity of cyanobacteria by as much as 56% during a 24-hour period. A reduction of chlorophyll equates to a reduction in photosynthetic behavior of the cyanobacteria.

The experimental data illustrates that UV-C power of approximately 48 watt-seconds in combination with microbubbles and sonification utilizing ultrasonic transducers in quite effective in mitigating cyanobacteria. A frequency of 28 kHz @ 0.75 watts was delivered via two ultrasonic transducers. This treatment produced a significant reduction in chlorophyll, measuring an approximate reduction of −96.5% after a 24-hour observation period.

In another example, the reduction of chlorophyll levels were examined for a duplicate experiment, however this time we examined the chlorophyll levels after a 72-hour observation period. The chlorophyll levels after 72 hours measured at 59% of their original baseline or pretreatment levels. This suggests that even after a three-day window the activity of the cyanobacteria is significantly lower than pretreatment levels.

The benchtop tests were utilized to provide an approximation of the mitigation levels that could be obtained in a operational device. One embodiment of an operational device comprises 32 UV-C lamps, configured in 2 rows of 16. Each lamp is a Rexim 6-watt hot filament lamp operating at 254 nm and when combined within the chamber it produced an accumulative value of 192 watts of UV-C light.

In one embodiment, the operational device is designed to traverse water at 1 mph, which given the size of the current chamber would produce a pass-through exposure time of 2.5 seconds. The approximate UV-C energy the cyanobacteria will likely encounter would then approximate to be 192 watts×2.5 seconds=480 watt-seconds of exposure.

The inventors performed all of the experiments to test for mitigation of cyanobacteria as described herein. In order to measure the results of the mitigation experiments, spectroscopic observation experiments (and the data described herein) were performed at SUNY ESF in Syracuse, N.Y. on samples provided by the inventors, comprising both control samples of unprocessed water and samples of processed water, and were supervised by their laboratory staff.

Wastewater

One important aspect of helping the environment is to remove total phosphorus (TP). TP in wastewater can be either reactive phosphorus or non-reactive phosphorus. The reactive phosphorus can be taken up by plants and algae. When there is too high of concentrations of phosphorus in the water column, these can lead to harmful algal blooms (HABs). By reducing the phosphorus content, one may mitigate algae, or prevent the algae from growing to the extent that they cause problems. This mitigation can be accomplished by removing a nutrient that the algae rely upon for growth.

By way of example, it is well known that the area east of Tampa Bay, Fla. is a major source of mined phosphate. When runoff which is rich in dissolved phosphorus from the phosphate waste holding ponds in that area reaches the Gulf of Mexico at Tampa Bay, there have been serious algal blooms that have persisted for extended lengths of time, creating problems for the local residents and killing many fish and other wildlife.

Experiments have also been conducted using the apparatus described hereinabove on wastewater samples taken from the Canastota Water Pollution Control Plant, in Canastota, N.Y. For these experiments there was no necessity to use the flotation sub-system, the propulsion sub-system, the locations sub-system and the aerial observation sub-system, because the wastewater plant is in a known location. In some embodiments, the use of the aqueous monitoring sub-system and the assessment sub-system is optional, depending on whether one wants to monitor the concentration of algae in the wastewater directly. The experiments were performed by extracting samples of raw wastewater, treating them in a bench-top apparatus, keeping a control sample, and then analyzing the results. Common methods of removing phosphorus involves a chemical precipitation with multivalent metal ions like calcium, aluminum, and iron. Finding a quick, efficient, and effective way to remove excess TP levels without adding excess chemicals would be ideal for local wastewater treatment plants.

Unexpectedly, it was found that the mitigation apparatus and methods described herein resulted in a significant reduction in phosphorus in the treated wastewater. In particular, the treatment of the wastewater using UV-C illumination, sonication and ozonation alone and in various combinations was performed. The reduction of phosphorus by UV-C alone amounted to about 60%, while reductions of about 30% were observed using the combinations of UV-C with ozone and sonication.

The wastewater was treated in the mitigation sub-system in a bench-top apparatus where various treatments were completed: UV-C alone, sonication alone, aeration alone, ozone alone, UV-C/sonication/aeration, and UV-C/sonication/ozone. Sonication consisted of sinusoidal frequencies ranging from 28 kHz to 35 kHz at 0.75 W radiating from two emitters located in the mitigation sub-system. Aeration consisted of an air pump with a flow rate of 2 L/min, which was introduced to the chamber through an air stone. Ozone was generated utilizing twin 185 nm UV lamps that shared the air stone at a combined flow rate of 2 L/min. Ozone levels introduced to the reactor at the time of treatment were approximately 3.4 ppm. The UV-C lamp contained a 6-watt hot filament lamp producing a measured intensity of 5.62 $\mu W/cm^2$ at the lamps surface at a frequency of 254 nm. All treatments were microprocessor controlled and in electrical communication with a laptop during each treatment to improve accuracy.

Post treatment, water was then collected in polypropylene bottles with sulfuric acid for preservation. Samples were sent to Pace Analytical Services, LLC, 575 Broad Hollow Road, Melville, N.Y. 11747 for TP analysis.

Definitions

Any reference in the claims to an electronic signal or an electromagnetic signal (or their equivalents) is to be understood that in a preferred embodiment the signal is a non-transitory electronic signal or a non-transitory electromagnetic signal. If the signal per se is not claimed, the reference may in some instances be to a description of a propagating or transitory electronic signal or electromagnetic signal.

Recording the results from an operation or data acquisition, such as for example, recording results at a particular frequency or wavelength, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use, so that the result can be displayed, recorded to a non-volatile memory, or used in further data processing or analysis.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

INCORPORATION BY REFERENCE

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. An apparatus configured to mitigate at least one of a harmful water-borne bacteria and a harmful chemical produced by the bacteria, comprising:
    an aqueous monitoring sub-system comprising at least one of a Phycocyanin Blue-Green Algae Sensor, a Phycoerythrin Blue-Green Algae Sensor and a Chlorophyll A sensor configured to measure a concentration of algae in a body of water and configured to provide a signal responsive to said concentration of said algae;
    an assessment sub-system in communication with said aqueous monitoring sub-system, said assessment sub-system configured to receive said signal from said aqueous monitoring sub-system, said assessment sub-system comprising a microprocessor upon which can operate a set of instructions recorded in non-volatile memory, said assessment sub-system configured to process said received signal and to provide a current value for a concentration of algae in said body of water, and configured to provide a predetermined reference concentration value;
    a mitigation sub-system comprising three reaction zones:
        a first reaction zone comprising a UV illumination source, a source of microbubbles, and an ultrasonic transducer configured to apply, respectively, one or more of a UV illumination, a microbubble and ultrasonic sound in the range of 28 kHz to 35 kHz to a quantity of said water to mitigate the growth of algae;
        a second reaction zone configured to provide a gas comprising ozone for reaction with a first aqueous effluent from said first reaction zone; and
        a third reaction zone comprising a UV-C illumination source configured to illuminate a second aqueous effluent from said second reaction zone to convert any residual ozone in said second aqueous effluent to molecular oxygen;
    a control sub-system in communication with said aqueous monitoring sub-system, said assessment sub-system and said mitigation sub-system and configured to compare said current value for said concentration of algae with said predetermined reference concentration value, and based on such comparison, is configured to control the operation of said sub-systems, and to record data provided by said sub-systems; and
    a communication sub-system in communication with said control sub-system, said communication sub-system configured to transmit said data to an operator of said apparatus and to receive instructions from said operator for communication to said control sub-system.

2. The apparatus of claim 1, configured to reduce an amount of a nutrient in said body of water to mitigate said growth of algae.

3. The apparatus of claim 2, wherein said nutrient in said body of water is phosphorus.

4. The apparatus of claim 1, further comprising:
    a flotation sub-system configured to allow said apparatus to operate as a water-going apparatus;
    a propulsion sub-system to allow said water-going apparatus to move relative to said body of water upon which it floats;
    a location sub-system configured to determine where said water-going apparatus is situated within said body of water;
    each of said flotation sub-system, said propulsion sub-system and said location sub-system in communication with said control sub-system.

5. The apparatus of claim 1, further comprising an aerial observation sub-system tethered to said water-going apparatus and configured to provide information about the area adjacent said water-going apparatus, said aerial observation system in communication with said control sub-system.

6. The apparatus of claim 1, configured to reduce in said body of water at least one of said concentration of said algae and an amount of said harmful chemical produced by said algae.

7. A method of mitigating at least one of a harmful water-borne bacteria and a harmful chemical produced by the bacteria, comprising the steps of:
    providing an apparatus comprising:
        an aqueous monitoring sub-system comprising at least one of a Phycocyanin Blue-Green Algae Sensor, a Phycoerythrin Blue-Green Algae Sensor and a Chlorophyll A sensor configured to measure a concentration of algae in a body of water and configured to provide a signal responsive to said concentration of said algae;
        an assessment sub-system in communication with said aqueous monitoring sub-system, said assessment sub-system configured to receive said signal from said aqueous monitoring sub-system, said assessment sub-system comprising a microprocessor upon which can operate a set of instructions recorded in non-volatile memory, said assessment sub-system configured to process said received signal and to provide a current value for a concentration of algae in said body of water, and configured to provide a predetermined reference concentration value;
        a mitigation sub-system comprising three reaction zones:
            a first reaction zone comprising a UV illumination source, a source of microbubbles, and an ultrasonic transducer configured to apply, respectively, one or more of a UV illumination, a microbubble and ultrasonic sound in the range of 28 kHz to 35 kHz to a quantity of said water to mitigate the growth of algae;
            a second reaction zone configured to provide a gas comprising ozone for reaction with a first aqueous effluent from said first reaction zone; and
            a third reaction zone comprising a UV-C illumination source configured to illuminate a second aqueous effluent from said second reaction zone to convert any residual ozone in said second aqueous effluent to molecular oxygen;
        a control sub-system in communication with said aqueous monitoring sub-system, said assessment sub-system and said mitigation sub-system and configured to compare said current value for said concentration of algae with said predetermined reference concentration value, and based on such comparison, is configured to control the operation of said sub-systems, and to record data provided by said sub-systems; and a communication sub-system in communication with said control sub-system, said communication sub-system configured to transmit said data to an operator of said apparatus and to receive instructions from said operator for communication to said control sub-system;

operating said apparatus to collect a quantity of water;

using said control sub-system to operate said first reaction zone of said mitigation sub-system to apply at least one of said UV illumination, said microbubble and said ultrasonic sound to said quantity of said water to reduce an amount of a nutrient;

using said control sub-system to operate said second reaction zone of said mitigation sub-system to apply ozone to a first aqueous effluent from said first reaction zone; and using said control sub-system to operate said third reaction zone to apply UV-C illumination to an aqueous effluent from said second reaction zone to convert any residual ozone to oxygen; and discharging an aqueous effluent from said third reaction zone into said body of water;

thereby mitigating at least one of said harmful water-borne bacterium and said harmful chemical produced by the bacteria without introducing ozone into said body of water.

8. The method of claim 7, wherein said nutrient is phosphorus.

9. The method of claim 7, wherein said apparatus further comprises:

a flotation sub-system configured to allow said apparatus to operate as a water-going apparatus;

a propulsion sub-system to allow said water-going apparatus to move relative to a said body of water upon which it floats;

a location sub-system configured to determine where said water-going apparatus is situated within said body of water;

each of said flotation sub-system, said propulsion sub-system and said location sub-system in communication with said control sub-system; and operating said water-going apparatus to mitigate at least one of said harmful water-borne bacterium and said harmful chemical produced by the bacteria without introducing ozone into said body of water.

10. The method of claim 9, wherein said apparatus further comprises an aerial observation sub-system tethered to said water-going apparatus and configured to provide information about the area adjacent said water-going apparatus, said aerial observation system in communication with said control sub-system.

* * * * *